(12) United States Patent
Barda et al.

(10) Patent No.: US 10,968,214 B2
(45) Date of Patent: Apr. 6, 2021

(54) KRAS G12C INHIBITORS

(71) Applicant: Eli Lilly and Company, Indianapolis, IN (US)

(72) Inventors: David Anthony Barda, Indianapolis, IN (US); David Andrew Coates, New Palestine, IN (US); Ryan James Linder, Carmel, IN (US); Sheng-Bin Peng, Carmel, IN (US); Mohammad Sadegh Zia-Ebrahimi, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 16/595,666

(22) Filed: Oct. 8, 2019

(65) Prior Publication Data
US 2020/0115375 A1    Apr. 16, 2020

Related U.S. Application Data

(60) Provisional application No. 62/745,502, filed on Oct. 15, 2018.

(51) Int. Cl.
| | | |
|---|---|---|
| C07D 239/72 | (2006.01) |
| A61K 31/517 | (2006.01) |
| A61P 35/00 | (2006.01) |
| C07D 417/14 | (2006.01) |
| C07K 16/28 | (2006.01) |

(52) U.S. Cl.
CPC ............ C07D 417/14 (2013.01); A61P 35/00 (2018.01); *C07B 2200/13* (2013.01); *C07K 16/2818* (2013.01); *C07K 16/2827* (2013.01); *C07K 16/2863* (2013.01)

(58) Field of Classification Search
CPC ...... C07D 239/72; A61K 31/517; A61P 35/00
USPC ....................................... 544/284; 514/266.2
See application file for complete search history.

(56) References Cited

FOREIGN PATENT DOCUMENTS

| WO | 2015054572 A1 | 4/2015 |
| WO | 2016044772 A1 | 3/2016 |
| WO | 2016164675 A1 | 10/2016 |

*Primary Examiner* — Raymond J Henley, III
(74) *Attorney, Agent, or Firm* — Cedric A. D'Hue

(57) ABSTRACT

The present invention provides compounds of the Formula I below

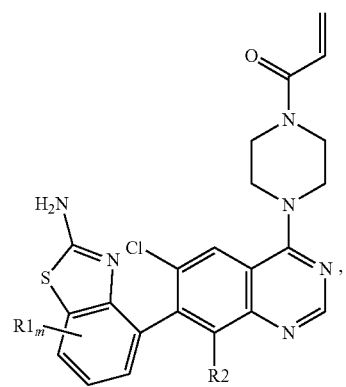

where R1, R2 and m are as described herein, pharmaceutically acceptable salts of the compounds of Formula 1, and methods of using these compounds and salts for treating patients for cancer.

26 Claims, No Drawings

KRAS G12C INHIBITORS

The present invention relates to novel 2-aminobenzothiazole compounds and pharmaceutically acceptable salts thereof, pharmaceutical compositions including the 2-aminobenzothiazole compounds and salts, and methods of using the compounds and salts to treat cancers such as lung cancer, colorectal cancer, pancreatic cancer, bladder cancer, cervical cancer, or esophageal cancer. The present invention also includes combinations of novel 2-aminobenzothiazole compounds with a CDK4 and CDK6 inhibitor abemaciclib, EGFR small molecule inhibitors, EGFR monoclonal antibody cetuximab, an anti-PD-1 antibody or an anti-PDL-1 antibody.

The MAPK/ERK signaling pathway relays extracellular stimuli to the nucleus, thereby regulating diverse cellular responses including cell proliferation, differentiation, and apoptosis. KRas protein is an initiator of the MAPK/ERK signaling pathway and functions as a switch responsible for inducing cell division. In its inactive state, KRas binds guanosine diphosphate (GDP), effectively sending a negative signal to suppress cell division. In response to an extracellular signal, KRas is allosterically activated allowing for nucleotide exchange of GDP for guanosine triphosphate (GTP). In its GTP-bound active state, KRas recruits and activates proteins necessary for the propagation of growth factor induced signaling, as well as other cell signaling receptors. Examples of the proteins recruited by KRas-GTP are c-Raf and PI3-kinase. KRas, as a GTP-ase, converts the bound GTP back to GDP, thereby returning itself to an inactive state, and again propagating signals to suppress cell division, KRas gain of function mutations exhibit an increased degree of GTP binding and a decreased ability to convert GTP into GDP. The result is an increased MAPK/ERK signal which promotes cancerous cell growth. Missense mutations of KRas at codon 12 are the most common mutations and markedly diminish GTPase activity.

Oncogenic KRas mutations have been identified in approximately 30% of human cancers, and demonstrated to activate multiple downstream signaling pathways. Despite the prevalence of KRas mutations, it has been a difficult therapeutic target. (Cox, A. D. *Drugging the Undruggable RAS: Mission Possible?* Nat. Rev. Drug Disc. 2014, 13, 828-851; Pylayeva-Gupta, y et al. *RAS Oncogenes: Weaving a Tumorigenic Web*. Nat. Rev. Cancer 2011, 11, 761-774).

WO2015/054572 and WO2016/164675 disclose certain quinazoline derivatives capable of binding to KRas G12C. WO2016/044772 also discloses methods of using such quanzoline derivatives.

There remains a need to provide alternative, small molecule KRas inhibitors. In particular, there is a need to provide more potent, orally deliverable KRas inhibitors that are useful for treating cancer. More particularly, there is a need to provide small molecule inhibitors that specifically inhibit KRas GTP activity. There is also a need to provide small molecule KRas inhibitors that exhibit greater efficacy at the same or reduced KRas inhibitory activity. Further, there is a desire to provide KRas inhibitors that exhibit better pharmacokinetic/pharmacodynamic properties. Also, there is a need to provide more potent KRas inhibitors that exhibit increased efficacy with reduced or minimized untoward effects. The present invention addresses one or more of these needs by providing novel KRas inhibitors.

The present invention provides a compound of the Formula I:

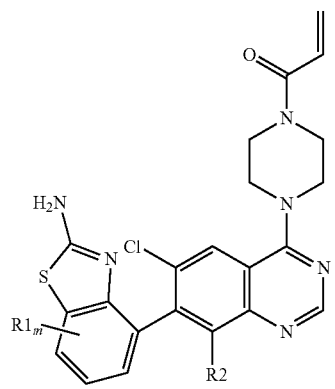

wherein m is 0-2; each R1 is F; and R2 is selected from: H, F, and Cl; or a pharmaceutically acceptable salt thereof. In one embodiment, R2 is F. In another embodiment, R2 is Cl. In another embodiment, m is 0. In another embodiment, m is 1. In another embodiment, the compound of Formula I is provided as a free base. In yet another embodiment, the compound of Formula I is provided as a pharmaceutically acceptable salt.

The present invention also provides a compound selected from any one of Formulae II-VII below:

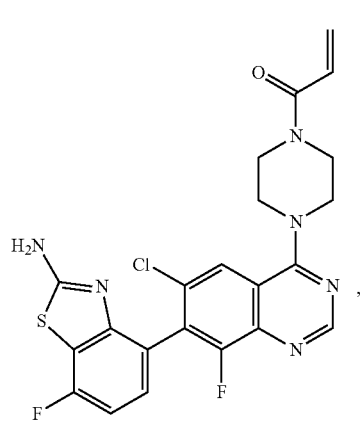

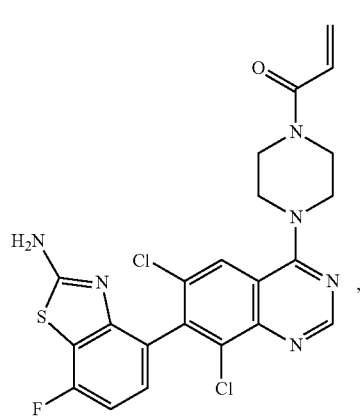

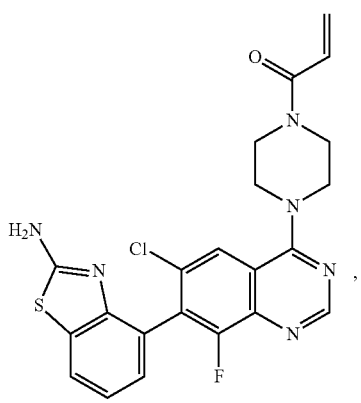
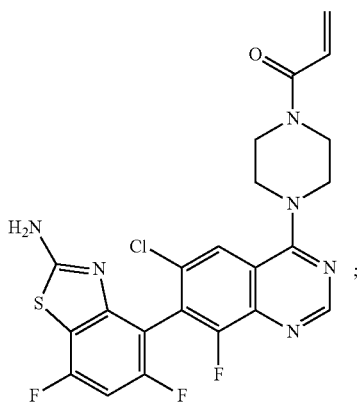
or a pharmaceutically acceptable salt thereof. In one embodiment, the compound of Formulae II-VII is provided as a pharmaceutically acceptable salt.
The present invention also provides a compound selected from any one of Formulae II, V, and VI:

-continued

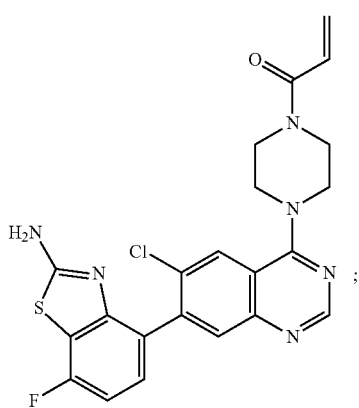

or a pharmaceutically acceptable salt thereof.

The present invention also provides a compound of Formula II which is:

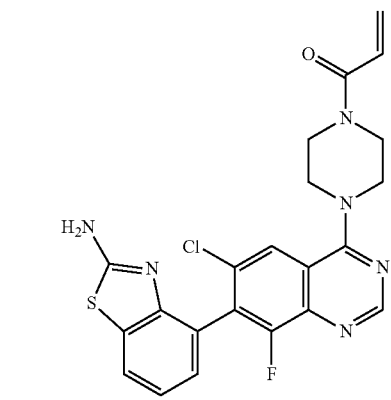

or a pharmaceutically acceptable salt thereof. In one embodiment, the compound of Formula II is provided as a pharmaceutically acceptable salt. In another embodiment, the salt of the compound of Formula II is a a hemi-malonate salt. In another embodiment, the salt of the compound of Formula II is a mesylate salt.

The present invention also provides a compound of Formula III which is:

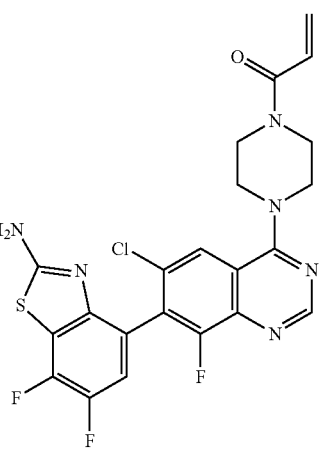

or a pharmaceutically acceptable salt thereof. In one embodiment, the compound of Formula III is provided as a pharmaceutically acceptable salt.

The present invention also provides a compound of Formula IV which is:

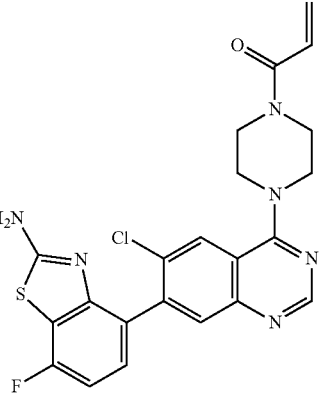

or a pharmaceutically acceptable salt thereof. In one embodiment, the compound of Formula IV is provided as a pharmaceutically acceptable salt.

The present invention also provides a compound of Formula V which is:

or a pharmaceutically acceptable salt thereof. In one embodiment, the compound of Formula V is provided as a pharmaceutically acceptable salt.

The present invention also provides a compound of Formula VI which is:

or a pharmaceutically acceptable salt thereof. In one embodiment, the compound of Formula VI is provided as a pharmaceutically acceptable salt.

The present invention also provides a compound of Formula VII which is:

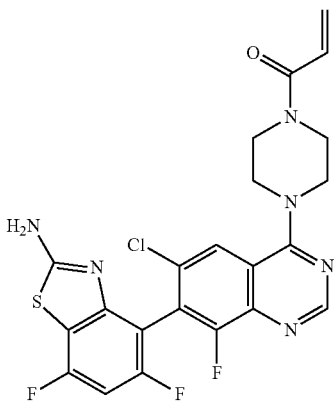

VII or a pharmaceutically acceptable salt thereof. In one embodiment, the compound of Formula VII is provided as a pharmaceutically acceptable salt.

The present invention also provides a compound of Formula VIII which is:

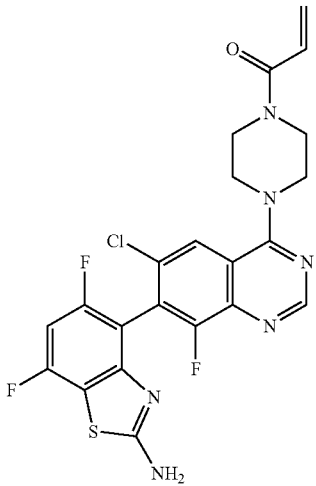

VIII or a pharmaceutically acceptable salt thereof. In one embodiment, the compound of Formula VIII is provided as a pharmaceutically acceptable salt.

The present invention also provides a compound of Formula IX which is:

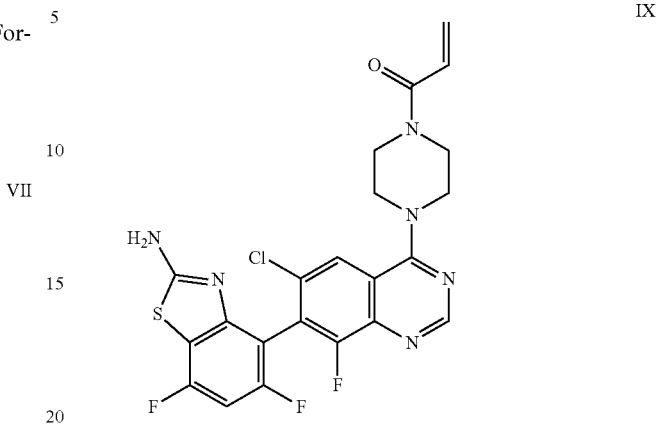

IX or a pharmaceutically acceptable salt thereof. In one embodiment, the compound of Formula IX is provided as a pharmaceutically acceptable salt.

The present invention also provides a compound of Formula II which is 1-{4-[7-(2-amino-7-fluoro-1,3-benzothiazol-4-yl)-6-chloro-8-fluoroquinazolin-4-yl]piperazin-1-yl}prop-2-en-1-one in a crystalline salt form. The present invention also provides crystalline 1-{4-[7-(2-amino-7-fluoro-1,3-benzothiazol-4-yl)-6-chloro-8-fluoroquinazolin-4-yl]piperazin-1-yl}prop-2-en-1-one hemi-malonate. The present invention also provides 1-{4-[7-(2-amino-7-fluoro-1,3-benzothiazol-4-yl)-6-chloro-8-fluoroquinazolin-4-yl]piperazin-1-yl}prop-2-en-1-one hemi-malonate in a crystalline form characterized by X-ray powder diffraction pattern having characteristic peaks using CuKα radiation, in 2θ±0.2°, occurring at 5.4° in combination with one or more of the peaks selected from the group consisting of 13.5°, 7.1°, and 23.0°. The present invention also provides crystalline 1-{4-[7-(2-amino-7-fluoro-1,3-benzothiazol-4-yl)-6-chloro-8-fluoroquinazolin-4-yl]piperazin-1-yl}prop-2-en-1-one mesylate. The present invention also provides 1-{4-[7-(2-amino-7-fluoro-1,3-benzothiazol-4-yl)-6-chloro-8-fluoroquinazolin-4-yl]piperazin-1-yl}prop-2-en-1-one mesylate in a crystalline form characterized by X-ray powder diffraction pattern having characteristic peaks using CuKα radiation, in 2θ±0.2°, occurring at 6.1° in combination with one or more of the peaks selected from the group consisting of 21.3°, 18.6°, and 19.8°.

The present invention also provides a pharmaceutical composition comprising a compound according to any one of Formulae I-IX, or a pharmaceutically acceptable salt thereof, and a pharmaceutically acceptable carrier, diluent, or excipient. Preferably, the compound is a compound of Formula II or a pharmaceutically acceptable salt thereof. Preferably, the salt of the compound of Formula II is a mesylate salt. Preferably, the salt of the compound of Formula II is a hemi-malonate salt.

The present invention also provides a method of treating cancer, comprising administering to a patient in need thereof, an effective amount of a compound according to any one of Formulae I-IX, or a pharmaceutically acceptable salt thereof. Preferably, the compound is a compound of Formula II or a pharmaceutically acceptable salt thereof. Preferably, the salt of the compound of Formula II is a mesylate salt. Preferably, the salt of the compound of Formula II is a hemi-malonate salt. In one embodiment, the cancer is lung cancer, colorectal cancer, pancreatic cancer, bladder cancer, cervical cancer, or esophageal cancer. In preferred embodiments the cancer is non-small cell lung cancer, pancreatic cancer, or colorectal cancer. In still more preferred embodiments, the cancer is non-small cell lung cancer. In another preferred embodiment the compound is a compound of Formula II, more preferably a mesylate salt of the compound of Formula II, even more preferably a crystalline mesylate salt of the compound of Formula II characterized by X-ray powder diffraction pattern having characteristic peaks using CuKα radiation, in 2θ±0.2°, occurring at 6.1° in combination with one or more of the peaks selected from the group consisting of 21.3°, 18.6°, and 19.8°, and the cancer is non-small cell lung cancer. In another preferred embodiment the compound is a compound of Formula II, more preferably a mesylate salt of the compound of Formula II, even more preferably a crystalline mesylate salt of the compound of Formula II characterized by X-ray powder diffraction pattern having characteristic peaks using CuKα radiation, in 2θ±0.2°, occurring at 6.1° in combination with one or more of the peaks selected from the group consisting of 21.3°, 18.6°, and 19.8°, and the cancer is pancreatic cancer. In another preferred embodiment the compound is a compound of Formula II, more preferably a mesylate salt of the compound of Formula II, even more preferably a crystalline mesylate salt of the compound of Formula II characterized by X-ray powder diffraction pattern having characteristic peaks using CuKα radiation, in 2θ±0.2°, occurring at 6.1° in combination with one or more of the peaks selected from the group consisting of 21.3°, 18.6°, and 19.8°, and the cancer is colorectal cancer.

The present invention also comprises a method of treating cancer, comprising administering to a patient in need thereof, an effective amount of a compound according to any one of Formulae I-IX, or a pharmaceutically acceptable salt thereof, in which the cancer has one or more cells that express a mutant KRas G12C protein. Preferably, the compound is a compound of Formula II or a pharmaceutically acceptable salt thereof. Preferably, the salt of the compound of Formula II is a mesylate salt. Preferably, the salt of the compound of Formula II is a hemi-malonate salt. In another embodiment, the cancer is non-small cell lung cancer, in which the cancer has one or more cells that express a KRas G12C mutant protein. In another embodiment, the cancer is colorectal cancer in which the cancer has one or more cells that express a KRas G12C mutant protein. In yet another embodiment, the cancer is pancreatic cancer in which the cancer has one or more cells that express a KRas G12C mutant protein. In another embodiment, the present invention comprising a method of treating KRas G12C mutant bearing cancers of other origins. In another preferred embodiment the compound is a compound of Formula II, more preferably a mesylate salt of the compound of Formula II, even more preferably a crystalline mesylate salt of the compound of Formula II characterized by X-ray powder diffraction pattern having characteristic peaks using CuKα radiation, in 2θ±0.2°, occurring at 6.1° in combination with one or more of the peaks selected from the group consisting of 21.3°, 18.6°, and 19.8°, and the cancer is non-small cell lung cancer, more preferably the non-small cell cancer has one or more cells that express a KRas G12C mutant protein. In another preferred embodiment the compound is a compound of Formula II, more preferably a mesylate salt of the compound of Formula II, even more preferably a crystalline mesylate salt of the compound of Formula II characterized by X-ray powder diffraction pattern having characteristic peaks using CuKα radiation, in 2θ±0.2°, occurring at 6.1° in combination with one or more of the peaks selected from the group consisting of 21.3°, 18.6°, and 19.8°, and the cancer is pancreatic cancer, more preferably the pancreatic cancer has one or more cells that express a KRas G12C mutant protein. In another preferred embodiment the compound is a compound of Formula II, more preferably a mesylate salt of the compound of Formula II, even more preferably a crystalline mesylate salt of the compound of Formula II characterized by X-ray powder diffraction pattern having characteristic peaks using CuKα radiation, in 2θ±0.2°, occurring at 6.1° in combination with one or more of the peaks selected from the group consisting of 21.3°, 18.6°, and 19.8°, and the cancer is colorectal cancer, more preferably the colorectal cancer has one or more cells that express a KRas G12C mutant protein.

The present invention also provides a method of modulating a mutant KRas G12C enzyme in a patient in need thereof, by administering a compound according to any one of Formulae I-IX, or a pharmaceutically acceptable salt thereof. Preferably, the compound is a compound of Formula II or a pharmaceutically acceptable salt thereof. Preferably, the salt of the compound of Formula II is a mesylate salt. Preferably, the salt of the compound of Formula II is a hemi-malonate salt. Preferably the method comprises inhibiting a human KRas G12C enzyme.

The present invention also provides a method of treating cancer in a patient in need thereof, wherein the patient has a cancer that was determined to express the KRas G12C mutant protein. Preferably, the compound is a compound of Formula II or a pharmaceutically acceptable salt thereof. Preferably, the salt of the compound of Formula II is a mesylate salt. Preferably, the salt of the compound of Formula II is a hemi-malonate salt. The method comprises administering to a patient an effective amount of a compound according to any one of Formulae I-IX, or a pharmaceutically acceptable salt thereof. The G12C mutational status of one or more cancer cells can be determined by a number of assays in the art. Typically, one or more biopsies containing one or more cancer cells are obtained, and subjected to sequencing and/or polymerase chain reaction (PCR). Circulating cell-free DNA can also be used, e.g. in advanced cancers. Non-limiting examples of sequencing and PCR techniques used to determine the mutational status (e.g. G12C mutational status, in one or more cancer cells or in circulating cell-free DNA) include direct sequencing, next-generation sequencing, reverse transcription polymerase chain reaction (RT-PCR), multiplex PCR, and pyrosequencing and multi-analyte profiling.

The present invention also provides a compound according to any one of Formulae I-IX for use in therapy. Preferably, the compound is a compound of Formula II or a pharmaceutically acceptable salt thereof. Preferably, the salt of the compound of Formula II is a mesylate salt. Preferably, the salt of the compound of Formula II is a hemi-malonate salt. The compound or a pharmaceutically acceptable salt thereof, can be for use in treating cancer. Preferably, the cancer is lung cancer, colorectal cancer, pancreatic cancer, bladder cancer, cervical cancer, or esophageal cancer. In preferred embodiments the cancer is non-small cell lung cancer, pancreatic cancer, or colorectal cancer. In still more preferred embodiments, the cancer is non-small cell lung cancer. In other embodiments, the cancer has one or more cancer cells that express the mutant KRas G12C protein. Preferably, the cancer is selected from: KRas G12C mutant non-small cell lung cancer, KRas G12C mutant colorectal cancer, and KRas G12C mutant pancreatic cancer. In another preferred embodiment, the compound is a compound of Formula II, more preferably a mesylate salt of the compound of Formula II, even more preferably a crystalline mesylate salt of the compound of Formula II characterized by X-ray powder diffraction pattern having characteristic peaks using CuKα radiation, in 2θ±0.2°, occurring at 6.1° in combination with one or more of the peaks selected from the group consisting of 21.3°, 18.6°, and 19.8°, and the cancer is non-small cell lung cancer, more preferably the non-small cell cancer has one or more cells that express a KRas G12C mutant protein. In another preferred embodiment, the compound is a compound of Formula II, more preferably a mesylate salt of the compound of Formula II, even more preferably a crystalline mesylate salt of the compound of Formula II characterized by X-ray powder diffraction pattern having characteristic peaks using CuKα radiation, in 2θ±0.2°, occurring at 6.1° in combination with one or more of the peaks selected from the group consisting of 21.3°, 18.6°, and 19.8°, and the cancer is pancreatic cancer, more preferably the pancreatic cancer has one or more cells that express a KRas G12C mutant protein. In another preferred embodiment, the compound is a compound of Formula II, more preferably a mesylate salt of the compound of Formula II, even more preferably a crystalline mesylate salt of the compound of Formula II characterized by X-ray powder diffraction pattern having characteristic peaks using CuKα radiation, in 2θ±0.2°, occurring at 6.1° in combination with one or more of the peaks selected from the group consisting of 21.3°, 18.6°, and 19.8°, and the cancer is colorectal cancer, more preferably the colorectal cancer has one or more cells that express a KRas G12C mutant protein.

The present invention also provides for the use of a compound according to any one of Formulae I-IX, or a pharmaceutically acceptable salt thereof, in the manufacture of a medicament for treating cancer. Preferably, the compound is a compound of Formula II or a pharmaceutically acceptable salt thereof. Preferably, the salt of the compound of Formula II is a mesylate salt. Preferably, the salt of the compound of Formula II is a hemi-malonate salt. Preferably, the cancer is lung cancer, colorectal cancer, pancreatic cancer, bladder cancer, cervical cancer, or esophageal cancer. In preferred embodiments, the cancer is non-small cell lung cancer, pancreatic cancer, or colorectal cancer. In still more preferred embodiments, the cancer is non-small cell lung cancer. In other embodiments, the cancer has one or more cancer cells that express the mutant KRas G12C protein. Preferably, the cancer is selected from KRas G12C mutant non-small cell lung cancer, KRas G12C mutant colorectal cancer, and KRas G12C mutant pancreatic cancer. In another preferred embodiment the compound is a compound of Formula II, more preferably a mesylate salt of the compound of Formula II, even more preferably a crystalline mesylate salt of the compound of Formula II characterized by X-ray powder diffraction pattern having characteristic peaks using CuKα radiation, in 2θ±0.2°, occurring at 6.1° in combination with one or more of the peaks selected from the group consisting of 21.3°, 18.6°, and 19.8°, and the cancer is non-small cell lung cancer, more preferably the non-small cell cancer has one or more cells that express a KRas G12C mutant protein. In another preferred embodiment, the compound is a compound of Formula II, more preferably a mesylate salt of the compound of Formula II, even more preferably a crystalline mesylate salt of the compound of Formula II characterized by X-ray powder diffraction pattern having characteristic peaks using CuKα radiation, in 2θ±0.2°, occurring at 6.1° in combination with one or more of the peaks selected from the group consisting of 21.3°, 18.6°, and 19.8°, and the cancer is pancreatic cancer, more preferably the pancreatic cancer has one or more cells that express a KRas G12C mutant protein. In another preferred embodiment, the compound is a compound of Formula II, more preferably a mesylate salt of the compound of Formula II, even more preferably a crystalline mesylate salt of the compound of Formula II characterized by X-ray powder diffraction pattern having characteristic peaks using CuKα radiation, in 2θ±0.2°, occurring at 6.1° in combination with one or more of the peaks selected from the group consisting of 21.3°, 18.6°, and 19.8°, and the cancer is colorectal cancer, more preferably the colorectal cancer has one or more cells that express a KRas G12C mutant protein.

The present invention also provides a combination comprising a compound according to any one of Formulae I-IX, or a pharmaceutically acceptable salt thereof and abemaciclib, or a pharmaceutically acceptable salt thereof, for simultaneous, separate, or sequential use in the treatment of cancer. Preferably, the compound is a compound of Formula II or a pharmaceutically acceptable salt thereof. Preferably, the salt of the compound of Formula II is a mesylate salt. Preferably, the salt of the compound of Formula II is hemi-malonate salt. In other embodiments, the cancer has one or more cancer cells that express the mutant KRas G12C protein. Preferably, the cancer is selected from KRas G12C mutant non-small cell lung cancer, KRas G12C mutant colorectal cancer, and KRas G12C mutant pancreatic cancer.

The present invention also provides a combination comprising a compound according to any one of Formulae I-IX, or a pharmaceutically acceptable salt thereof and an EGFR inhibitor, or a pharmaceutically acceptable salt thereof, for simultaneous, separate, or sequential use in the treatment of cancer. Preferably, the compound is a compound of Formula II or a pharmaceutically acceptable salt thereof. Preferably, the salt of the compound of Formula II is a mesylate salt. Preferably, the salt of the compound of Formula II is a hemi-malonate salt. Preferably, the EGFR inhibitor is erlotinib. Preferably, the EGFR inhibitor is afatinib. Preferably, the EGFR inhibitor is cetuximab. In other embodiments, the cancer has one or more cancer cells that express the mutant KRas G12C protein. Preferably, the cancer is selected from KRas G12C mutant non-small cell lung cancer, KRas G12C mutant colorectal cancer, and KRas G12C mutant pancreatic cancer.

The present invention also provides a combination comprising a compound according to any one of Formulae I-IX, or a pharmaceutically acceptable salt thereof and an anti-programmed cell death antibody for simultaneous, separate, or sequential use in the treatment of cancer. Preferably, the compound is a compound of Formula II or a pharmaceutically acceptable salt thereof. Preferably, the salt of the compound of Formula II is a mesylate salt. Preferably, the salt of the compound of Formula II is a hemi-malonate salt. In other embodiments, the cancer has one or more cancer cells that express the mutant KRas G12C protein. Preferably, the cancer is selected from KRas G12C mutant non-small cell lung cancer, KRas G12C mutant colorectal cancer, and KRas G12C mutant pancreatic cancer.

The term "pharmaceutically acceptable salt" as used herein refers a salt of a compound that is considered to be acceptable for clinical and/or veterinary use. Examples of pharmaceutically acceptable salts and common methodology for preparing them can be found in "Handbook of Pharmaceutical Salts: Properties, Selection and Use" P. Stahl, et al., 2nd Revised Edition, Wiley-V C H, 2011 and S. M. Berge, et al., "Pharmaceutical Salts", *Journal of Pharmaceutical Sciences*, 1977, 66(1), 1-19.

The pharmaceutical compositions for the present invention may be prepared using pharmaceutically acceptable additives. The term "pharmaceutically acceptable additive(s)" as used herein for the pharmaceutical compositions, refers to one or more carriers, diluents, and excipients that are compatible with the other additives of the composition or formulation and not deleterious to the patient. Examples of pharmaceutical compositions and processes for their preparation can be found in "Remington: The Science and Practice of Pharmacy", Loyd, V., et al. Eds., 22$^{nd}$ Ed., Mack Publishing Co., 2012. Non-limiting examples of pharmaceutically acceptable carriers, diluents, and excipients include the following: saline, water, starch, sugars, mannitol, and silica derivatives; binding agents such as carboxymethyl cellulose, alginates, gelatin, and polyvinyl-pyrrolidone; kaolin and bentonite; and polyethyl glycols.

As used herein, the term "effective amount" refers to an amount that is a dosage, which is effective in treating a disorder or disease, such as a cancerous lesion or progression of abnormal cell growth and/or cell division. The attending physician, as one skilled in the art, can readily determine an effective amount by the use of conventional techniques and by observing results obtained under analogous circumstances. Dosages per day of treatment normally fall within a range of between about 1 mg per day or twice daily and 1000 mg per day or twice daily, more preferably 100 mg per day or twice daily and 900 mg per day or twice daily. Factors considered in the determination of an effective amount or dose of a compound include: whether the compound or its salt will be administered; the co-administration of other agents, if used; the species of patient to be treated; the patient's size, age, and general health; the degree of involvement or stage and/or the severity of the disorder; the response of the individual patient; the mode of administration; the bioavailability characteristics of the preparation administered; the dose regimen selected; and the use of other concomitant medication.

A treating physician, veterinarian, or other medical person will be able to determine an effective amount of the compound for treatment of a patient in need. Preferred pharmaceutical compositions can be formulated as a tablet or capsule for oral administration, a solution for oral administration, or an injectable solution. The tablet, capsule, or solution can include a compound of the present invention in an amount effective for treating a patient in need of treatment for cancer.

As used herein, the terms "treating", "to treat", or "treatment", includes slowing, reducing, or reversing the progression or severity of an existing symptom, disorder, condition, which can include specifically slowing the growth of a cancerous lesion or progression of abnormal cell growth and/or cell division.

As used herein, the term "patient" refers to a mammal in need of treatment. Preferably, the patient is a human that is in need of treatment for cancer, for example, KRas G12C mutant bearing cancers.

Certain abbreviations are defined as follows: "AcOH" refers to acetic acid; "ACN" refers to acetonitrile; "DCM" refers to dichloromethane; "DIPEA" refers to N,N-diisopropyl ethylamine; "DMAP" refers to 4-dimethylaminopyridine; "DMF" refers to N,N-dimethylformamide; "DMSO" refers to dimethylsulfoxide; "DTT" refers to dithiothreitol; "EDTA" refers to ethylenediaminetetraacetic acid; "EGTA" refers to ethylene glycol-bis(β-aminoethyl ether)-N,N,N',N'-tetraacetic acid; "ELISA" refers to enzyme-linked immunosorbent assay; "Et$_2$O" refers to diethyl ether; "EtOAc" refers to ethyl acetate; "FBS" refers to fetal bovine serum; "HPLC" refers to high-performance liquid chromatography; "h", "hr" or "hrs" refers to hour(s); "HRP" refers to horseradish peroxidase; "IPA" refers to isopropyl alcohol; "LC-ES/MS" refers to liquid chromatograph-electrospray mass spectrometry; "LC-MS" refers to liquid chromatography mass spectrometry; "MeOH" refers to methanol; "min" or "mins" refers to minute(s); "MTBE" refers to methyl tert-butyl ether; "NaOAc" refers to sodium acetate; "NaOMe" refers to sodium methoxide; "NMP" refers to 1-methylpyrrolidin-2-one; "PCR" refers to polymerase chain reaction; "RT" or "rt" refers to room temperature; "THF" refers to tetrahydrofuran; "TEA" refers to trimethylamine; "TF$_2$O" refers to trifluoromethanesulfonic anhydride; "TFA" refers to trifluoroacetic acid.

Individual isomers, enantiomers, diastereomers, and atropisomers may be separated or resolved by at any convenient point in the synthesis of compounds listed below, by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994). The present invention includes certain compounds, which are atropisomers and which can exist in different conformations or as different rotomers. Atropisomers are compounds, which exist in different conformations arising from restricted rotation about a single bond. Atropisomers can be isolated as separate chemical species if the energy barrier to rotation about the single is sufficiently high enough and the rate of interconversion is slow enough to allow the individual rotomers to be separated from each other.

A compound of any one of Formulae I-IX is readily converted to and may be isolated as a pharmaceutically acceptable salt. Salt formation can occur upon the addition of a pharmaceutically acceptable acid to form the acid addition salt. Salts can also form simultaneously upon deprotection of a nitrogen or oxygen, i.e., removing the protecting group. Examples, reactions and conditions for salt formation can be found in Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977). Preferably, the salt is a mesylate salt. Preferably, the salt is a hemi-malonate salt.

The compounds of the present invention, or salts thereof, may be prepared by a variety of procedures, some of which are illustrated in the Preparations and Examples below. The specific synthetic steps for each of the routes described may be combined in different ways, or in conjunction with steps from different routes, to prepare compounds or salts of the present invention. The products of each step in the Preparations below can be recovered by conventional methods, including extraction, evaporation, precipitation, chromatography, filtration, trituration, and crystallization.

Scheme 1

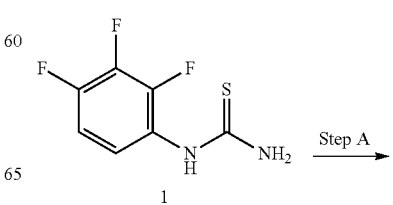

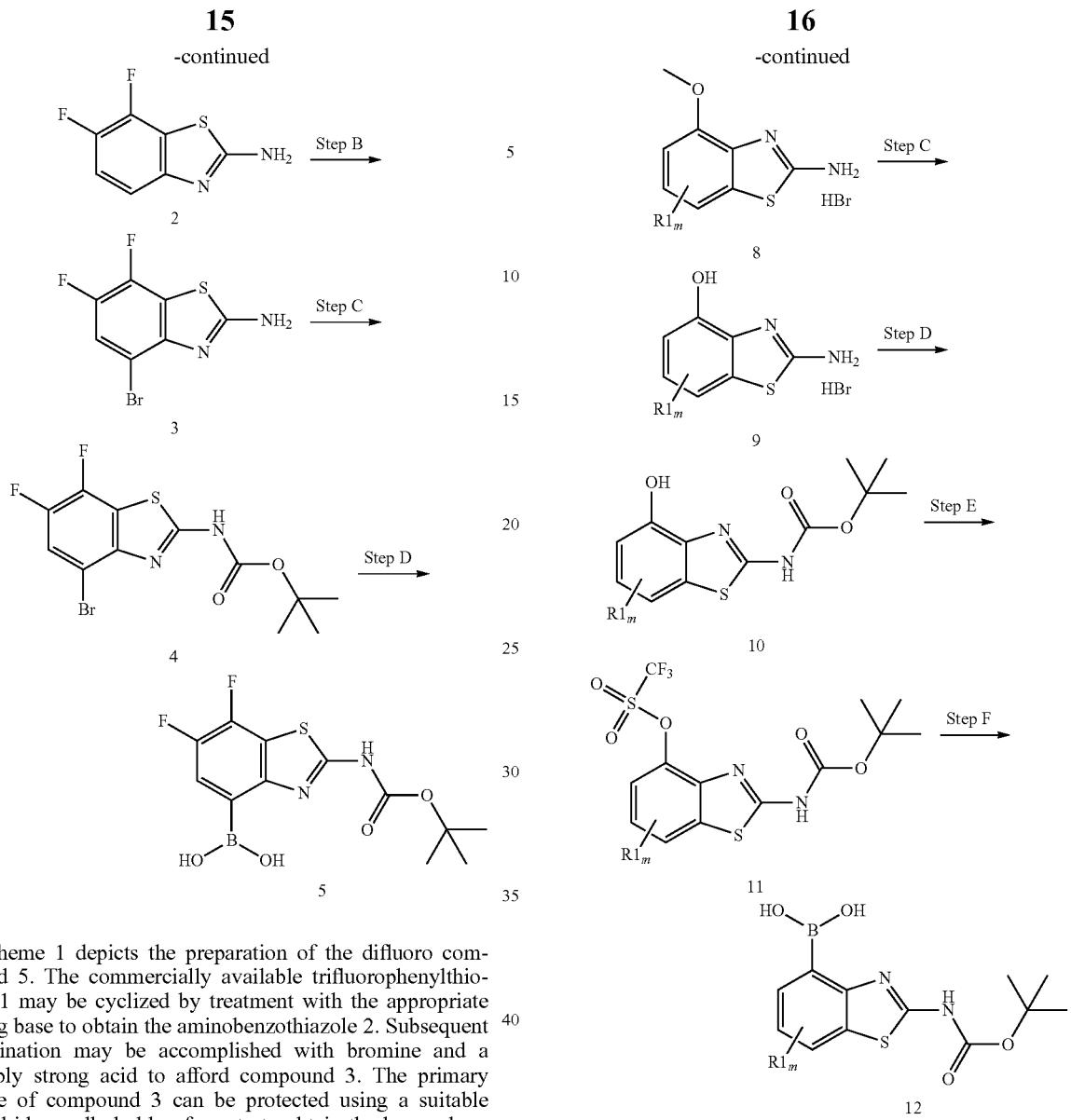

Scheme 1 depicts the preparation of the difluoro compound 5. The commercially available trifluorophenylthiourea 1 may be cyclized by treatment with the appropriate strong base to obtain the aminobenzothiazole 2. Subsequent bromination may be accomplished with bromine and a suitably strong acid to afford compound 3. The primary amine of compound 3 can be protected using a suitable anhydride or alkyl chloroformate to obtain the bromo benzothizole compound 4. Bromobenzothiazole 4 may be functionalized to the boronic acid 5 with the appropriate borate and lithiating reagent.

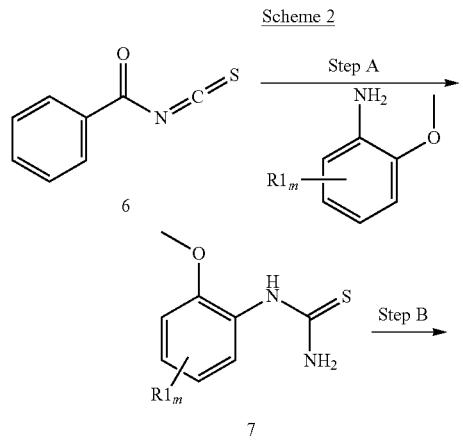

Scheme 2 depicts the preparation of the boronic acid 12, where m=0-2 and R1 is F. Thiourea formation from the commercially available benzoyl isothiocyante 6 may be accomplished by treatment with the acceptably substituted and commercially available methoxy-aniline, while maintaining a cool reaction temperature, to afford thiourea 7. Cyclization may be accomplished by refluxing thiourea 7 in chloroform following the addition of bromine to provide methoxy aminobenzothiazole 8. Demethylation and N-protection of 8 may be achieved by addition of BBr$_3$ while maintaining a cold reaction mixture under an inert atmosphere, followed by protection of the primary amine to provide the N-protected aminobenzothiazole 10. The N-protected aminobenzothiazole 10 may be treated with a base and an appropriate sulfonic anhydride or sulfonyl chloride to furnish the trifluoromethanesulfonate 11. Transformation of the trifluoromethanesulfonate to the boronic acid may be carried out utilizing a variety of metal catalysts, bases, and boronic ester or acid sources to provide aminobenzothiazole boronic acid 12.

Scheme 3

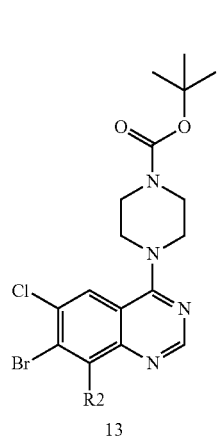

13

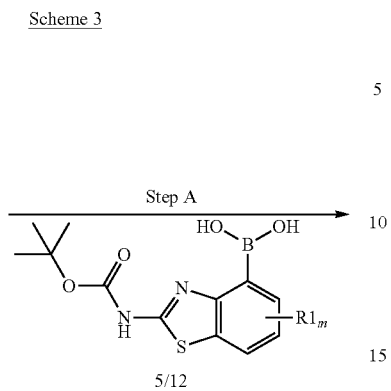

Step A →

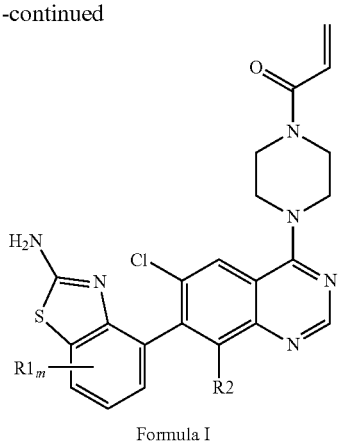

Formula I m = 0-2, R1 = F, R2 = H, F, Cl

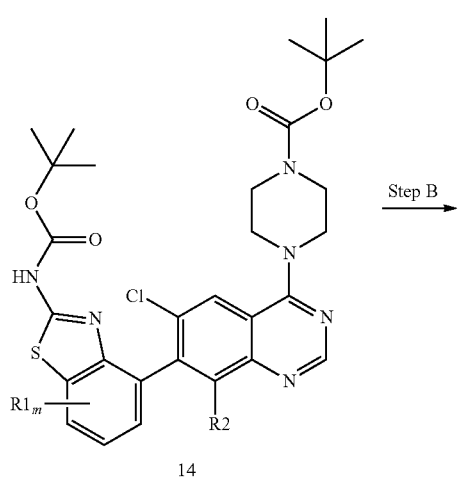

14

Step B →

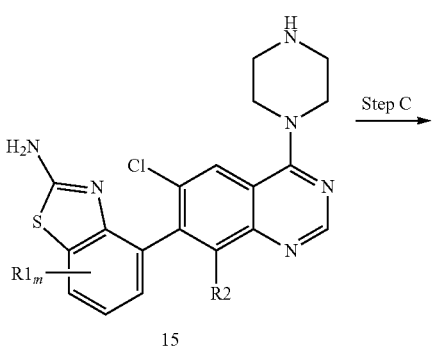

15

Step C →

Scheme 3 depicts the preparation of compound Formula I where m is 0-2, R1 is F and R2 is H, F, or Cl. The starting piperazine quinazoline, 13, may be prepared as described in U.S. Pat. No. 9,840,516. A Suzuki coupling may be employed using compound 13 and either compound 5 from Scheme 1 or compound 12 from Scheme 2 to provide the substituted quinazoline 14. Deprotection of both amines on compound 14 provides the intermediate 15. Finally, a compound according to Formula I may be formed by treatment of diamine 15 with base in either a polar aprotic or protic solvent and the appropriate acid chloride.

PREPARATIONS AND EXAMPLES

The following Preparations and Examples further illustrate the invention and represent typical synthesis of the compounds of the invention, but should not be construed to limit the scope of the invention in any way. The reagents and starting materials are readily available or may be readily synthesized either by known procedures or by employing various modifications, which may be made by one of ordinary skill in the art.

Compounds can be characterized by liquid chromatograph-electrospray mass spectrometry (LC-ES/MS) performed on an Agilent HP1100 liquid chromatography system. Electrospray mass spectrometry measurements (acquired in positive and/or negative mode) are performed on a Mass Selective Detector quadrupole mass spectrometer interfaced to the HP1100 HPLC. LC-MS conditions (low pH): column: PHENOMENEX® GEMINI® NX C-18 2.1× 50 mm 3.0 µm; gradient: 5-100% B in 3 min, then 100% B for 0.75 min column temperature: 50° C.+/−10° C.; flow rate: 1.2 mL/min; Solvent A: deionized water with 0.1% HCOOH; Solvent B: ACN with 0.1% formic acid; wavelength 214 nm. Alternate LC-MS conditions (high pH): column: WATERS™ XTERRA® MS C-18 columns 2.1×50 mm, 3.5 m; gradient: 5% of solvent A for 0.25 min, gradient from 5% to 100% of solvent B in 3 min and 100% of solvent B for 0.5 min or 10% to 100% of solvent B in 3 min and at 100% of solvent B for 0.75 min; column temperature: 50° C.+/−10° C.; flow rate: 1.2 mL/min; Solvent A: 10 mM NH₄HCO₃ pH 9; Solvent B: ACN wavelength: 214 nm.

Preparative reversed phase chromatography is performed on an Agilent 1200 LC-ES/MS equipped with a Mass Selective Detector mass spectrometer and a Leap autosampler/fraction collector. High pH methods are run on a 75×30 mm PHENOMENEX® GEMINI®-NX, 5 µm particle size column with a 10×20 mm guard. Flow rate of 85 mL/min. Eluent is 10 mM ammonium bicarbonate (pH 10) in ACN.

Preparation 1

6,7-Difluoro-1,3-benzothiazol-2-amine

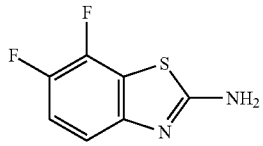

Combine NaH (14.6 g, 1.5 eq) and NMP (400 mL) under N₂. Add (2,3,4-trifluorophenyl)thiourea (50.0 g, 243 mmol) in ~5 g portions every 3-4 min. Stir at RT for two hr, then at 100° C. for 90 min. Cool to RT and pour the reaction mixture into ice/water (2.5 L). Add MTBE and separate the layers. Dry the organic layer over anhydrous Na₂SO₄, filter, and concentrate the filtrate in vacuo. Dilute with DCM (75 mL), then hexanes (425 mL). Sonicate, filter, wash with hexanes, and dry under vacuum to give the title compound as an off-white solid (33.5 g, 74%). MS (ES) m/z=187 (M+H).

Preparation 2

4-Bromo-6,7-difluoro-1,3-benzothiazol-2-amine

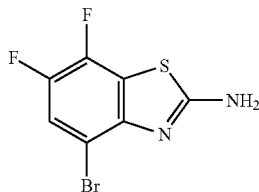 [SMILES: Nc1nc2c(Br)cc(F)c(F)c2s1]

Add NaOAc (31.0 g, 2.0 eq) to a solution of 6,7-difluoro-1,3-benzothiazol-2-amine (35.0 g, 188 mmol) in AcOH (625 mL). Add bromine (1.0 M in AcOH, 230 mL, 1.2 eq) dropwise over 75 min. Stir at RT for three hr. Concentrate the reaction mixture in vacuo to near dryness. Dilute with water (1.4 L), MTBE (1 L), and EtOAc (800 mL). Separate the layers. Wash the organics with saturated aqueous NaCl. Combine the aqueous layers with EtOAc. Separate the layers. Combine the aqueous layers with MTBE. Separate the layers. Dry the combined organics over anhydrous Na₂SO₄, filter, and concentrate in vacuo. Dilute with DCM (150 mL) and sonicate. Concentrate the mixture in vacuo to ~100 mL and cool to RT. Filter, wash with hexanes, and dry under vacuum to give the title compound as an off-white solid (44.4 g, 89%). MS (ES) m/z=($^{79}$Br/$^{81}$Br) 265/267 (M+H).

Preparation 3 tert-Butyl (4-bromo-6,7-difluoro-1,3-benzothiazol-2-yl)carbamate

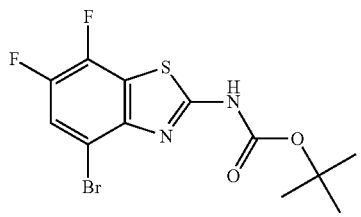 [SMILES: CC(C)(C)OC(=O)Nc1nc2c(Br)cc(F)c(F)c2s1]

Add DMAP (0.4 g, 0.02 eq) and DIPEA (35 mL, 1.2 eq) to a solution of 4-bromo-6,7-difluoro-1,3-benzothiazol-2-amine (44.4 g, 168 mmol) in THF (1 L). Place under N₂. Add di-tert-butyl dicarbonate (42.5 g, 1.2 eq). Stir at RT for 2.5 hr. Add MeOH (50 mL) and saturated aqueous NaHCO₃ (100 mL). Concentrate the reaction mixture in vacuo to near dryness. Dilute with water (700 mL) and saturated aqueous NaHCO₃ (150 mL). Add MTBE (750 mL) and separate the layers. Wash the organic layer with saturated aqueous NaCl. Dry the organic layer over anhydrous Na₂SO₄, filter, and concentrate the filtrate in vacuo to give the title compound as a yellow solid (60.6 g, 99%). MS (ES) m/z=($^{79}$Br/$^{81}$Br) 363/365 (M−H).

Preparation 4

{2-[(tert-Butoxycarbonyl)amino]-6,7-difluoro-1,3-benzothiazol-4-yl}boronic acid

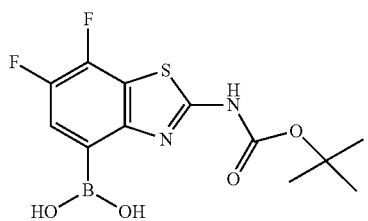 [SMILES: CC(C)(C)OC(=O)Nc1nc2c(B(O)O)cc(F)c(F)c2s1]

Add tert-butyl (4-bromo-6,7-difluoro-1,3-benzothiazol-2-yl)carbamate (2.0 g, 5.5 mmol) to a flask. Purge with N₂ and add THF (27 mL). Add triisopropyl borate (3.8 mL, 3.0 eq). Cool to −78° C. under N₂. Add n-butyllithium (2.5 M in hexanes, 6.6 mL, 3.0 eq) dropwise, maintaining the internal reaction temperature below −60° C. Warm to −30° C. to −35° C. over 30 min. Stir at −30° C. for 30 min. Quench with saturated aqueous NH₄Cl. Dilute with DCM and water. Separate the layers. Wash the organics with saturated aqueous NaCl. Dry the organics over Na₂SO₄, filter, and concentrate the filtrate in vacuo. Dilute with hexanes and sonicate. Heat to 50° C. and cool to RT. Filter to collect the title compound as a white solid (1.2 g, 65%). MS (ES) m/z=331 (M+H).

Preparation 5

N-(5-Fluoro-2-methoxyphenyl)thiourea

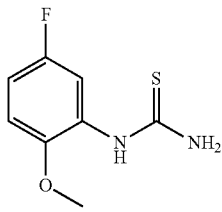

Combine benzoyl isothiocyanate (110 g, 671 mmol) and THF (875 mL). Cool to 5° C. under N$_2$. Add 5-fluoro-2-methoxyaniline (83.2 mL, 1.05 eq) dropwise, maintaining the internal reaction temperature below 10° C. Warm to RT and stir for 30 min. Add 5 M aqueous NaOH (161 mL, 1.20 eq) and water (200 mL). Heat at reflux for 3.5 hr. Add water (500 mL) and isopropyl acetate (800 mL). Cool to RT. Add concentrated aqueous HCl to adjust the pH to ~9-10. Separate the layers. Dry the organic layer over anhydrous MgSO$_4$, filter, and concentrate the filtrate in vacuo. Add EtOAc (360 mL) and hexanes (840 mL). Heat at reflux for five min. Cool to −20° C. and let sit overnight. Filter and wash the collected solid with cold hexanes to give the title compound as a colorless solid (118 g, 88%). MS (ES) m/z=201 (M+H).

Preparation 6

N-(3,5-Difluoro-2-methoxyphenyl)thiourea

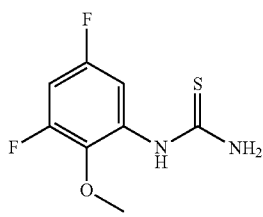

Combine benzoyl isothiocyanate (3.2 mL, 24 mmol) and THF (100 mL). Add 3,5-difluoro-2-methoxyaniline (4.0 g, 1.0 eq) dropwise. Stir at RT for three hr. Concentrate the reaction mixture in vacuo. Add THF (100 mL) and 1 M aqueous NaOH (14 mL, 1.2 eq). Heat at 80° C. overnight. Concentrate the reaction mixture in vacuo. Dilute with 1:1 EtOAc:DCM, sonicate, and filter. Concentrate the filtrate in vacuo. Purify by normal phase chromatography, eluting with a 0-50% EtOAc in DCM gradient, to give the title compound (3.5 g, 67%). MS (ES) m/z=219 (M+H).

Preparation 7

7-Fluoro-4-methoxy-1,3-benzothiazol-2-amine hydrogen bromide

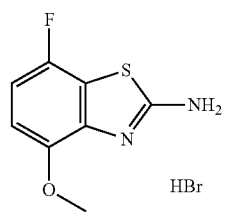

Combine N-(5-fluoro-2-methoxyphenyl)thiourea (118 g, 571 mmol) and CHCl$_3$ (2 L). Cool to 5° C. under N$_2$. Add Br$_2$ (30.1 mL, 1.02 eq) dropwise, maintaining the internal reaction temperature below 7° C. Stir at 0° C. for 30 min. Heat at reflux for 2.25 hrs. Cool to −20° C. and let sit overnight. Filter and wash with cold hexanes to give the title compound as a yellow solid (141 g, 89%). MS (ES) m/z=199 (M+H).

Preparation 8

5,7-Difluoro-4-methoxy-1,3-benzothiazol-2-amine hydrogen bromide

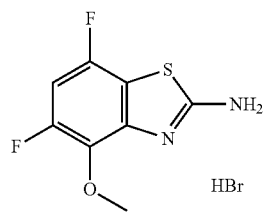

Prepare the title compound in a manner analogous to the method described in Preparation 7. MS (ES) m/z 217 (M+H).

Preparation 9

2-Amino-5,7-difluoro-1,3-benzothiazol-4-ol

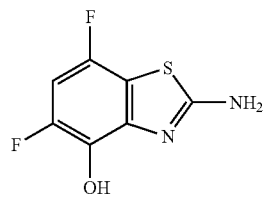 [SMILES: Nc1nc2c(O)c(F)cc(F)c2s1]

Combine 5,7-difluoro-4-methoxy-1,3-benzothiazol-2-amine hydrogen bromide (4.0 g, 13 mmol) and DCM (70 mL). Cool to 0° C. Add BBr$_3$ (1.0 M in DCM, 34 mL, 2.5 eq). Allow to slowly warm to RT and stir overnight. Quench carefully with MeOH (100 mL). Stir at RT for 30 min. Dilute with saturated aqueous NaHCO$_3$. Stir at RT for 30 min.

Filter to give the title compound as a white solid (2.7 g, 92%). MS (ES) m/z=203 (M+H).

Preparation 10 tert-Butyl (5,7-difluoro-4-hydroxy-1,3-benzothiazol-2-yl)carbamate

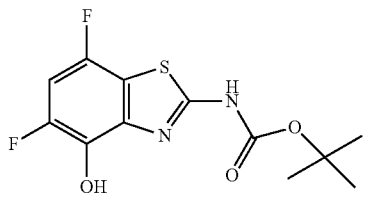 [SMILES: CC(C)(C)OC(=O)Nc1nc2c(O)c(F)cc(F)c2s1]

Combine 2-amino-5,7-difluoro-1,3-benzothiazol-4-ol (2.5 g, 12 mmol) and THF (60 mL). Add TEA (3.4 mL, 2.0 eq), DMAP (0.3 g, 0.2 eq) and di-tert-butyl dicarbonate (4.2 g, 1.5 eq). Stir at RT overnight. Concentrate the reaction mixture in vacuo. Add MeOH (60 mL) and NaOMe (3.4 g, 5.0 eq). Stir at RT overnight. Pour into a mix of ice/water. Filter to remove solids. Add concentrated aqueous HCl to the filtrate to adjust the pH to ~5. Dilute with DCM. Separate the layers. Dry the organics over anhydrous sodium sulfate, filter, and concentrate in vacuo to give the title compound as a light brown solid (1.4 g, 31%). MS (ES) m/z=301 (M–H).

Preparation 11

2-Amino-7-fluoro-1,3-benzothiazol-4-ol hydrogen bromide

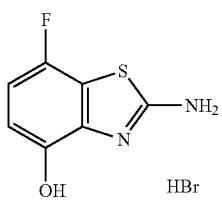 [SMILES: Nc1nc2c(O)ccc(F)c2s1 ; Br]

Cool DCM (1.5 L) to 0° C. under $N_2$. Add $BBr_3$ (150 mL, 3.1 eq) via a cannula. Add 7-fluoro-4-methoxy-1,3-benzothiazol-2-amine hydrogen bromide (141 g, 506 mmol) portion wise over 15 min. Allow the reaction mixture to slowly warm to RT and stir overnight. Cool to 0° C. and quench carefully with MeOH, maintaining the internal temperature below 10° C. Allow the gas output to bubble into cold 5 M aqueous NaOH. Filter and wash the collected solid with cold DCM to give the title compound as a colorless solid (117 g, 87%). MS (ES) m/z=185 (M+H).

Preparation 12 tert-Butyl (7-fluoro-4-hydroxy-1,3-benzothiazol-2-yl)carbamate

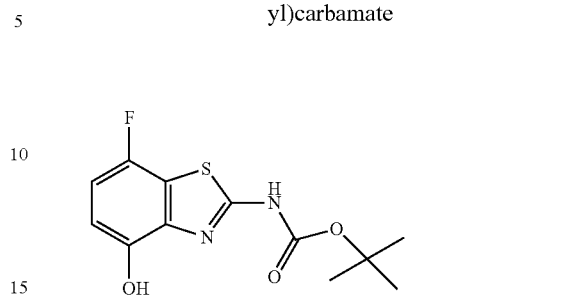

Combine 2-amino-7-fluoro-1,3-benzothiazol-4-ol hydrogen bromide (117 g, 441 mmol) and 1,4-dioxane (1.5 L). Cool to 10° C. Add TEA (129 mL, 2.1 eq) and maintain the internal reaction temperature below 15° C. Add DMAP (2.7 g, 0.05 eq) and di-tert-butyl dicarbonate (228 g, 2.3 eq). Allow the reaction mixture to slowly warm to RT and stir for two days. Dilute with water, EtOAc, and saturated aqueous NaCl. Separate the layers. Collect and concentrate the organic layer in vacuo. Add MeOH (900 mL) and NaOMe (5 M in MeOH, 132 mL, 1.5 eq). Stir at RT overnight. Add additional NaOMe (5 M in MeOH, 10 mL, 0.11 eq). Stir at RT for three hr. Concentrate in vacuo. Dilute with water and EtOAc. Separate the layers. Dry the organic layer over anhydrous $MgSO_4$, filter, and concentrate the filtrate in vacuo until solids form. Dilute with hexanes. Filter and wash the collected solid with hexanes to give the title compound as a light tan solid (97.2 g, 78%). MS (ES) m/z=283 (M–H).

Preparation 13

2-[(tert-Butoxycarbonyl)amino]-7-fluoro-1,3-benzothiazol-4-yl trifluoromethanesulfonate

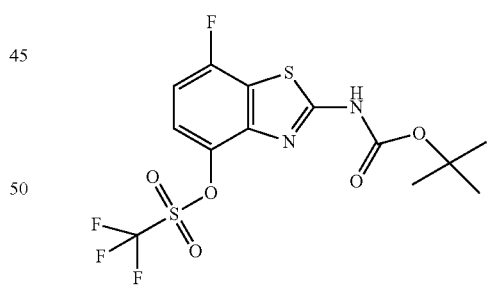

Combine tert-butyl (7-fluoro-4-hydroxy-1,3-benzothiazol-2-yl)carbamate (116 g, 407 mmol), DCM (1.4 L), and pyridine (66 mL, 2.0 eq). Cool to 5° C. under $N_2$. Add $TF_2O$ (83 mL, 1.2 eq) dropwise while maintaining the internal reaction temperature below 10° C. Dilute with water. Separate the layers. Wash the organic layer with 10% aqueous citric acid. Dry the organic layer over anhydrous $MgSO_4$, filter, and concentrate the filtrate in vacuo. Purify by normal phase chromatography, eluting with a 25-28% B in A gradient (A: hexanes, B: 25% DCM in EtOAc), to give the title compound as a yellow solid (123 g, 73%). MS (ES) m/z=415 (M–H).

Preparation 14

2-[(tert-Butoxycarbonyl)amino]-5,7-difluoro-1,3-benzothiazol-4-yl trifluoromethanesulfonate

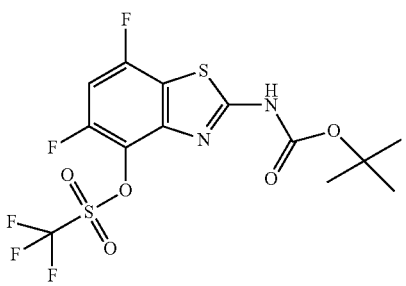 [SMILES: CC(C)(C)OC(=O)Nc1nc2c(OS(=O)(=O)C(F)(F)F)c(F)cc(F)c2s1]

Prepare the title compound in a manner analogous to the method described in Preparation 13. MS (ES) m/z 433 (M+H).

Preparation 15

{2-[(tert-Butoxycarbonyl)amino]-5,7-difluoro-1,3-benzothiazol-4-yl}boronic acid

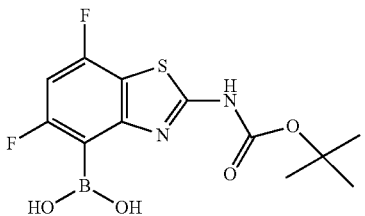 [SMILES: CC(C)(C)OC(=O)Nc1nc2c(B(O)O)c(F)cc(F)c2s1]

Combine 2-[(tert-butoxycarbonyl)amino]-5,7-difluoro-1,3-benzothiazol-4-yl trifluoromethanesulfonate (1.7 g, 3.9 mmol), potassium acetate (1.1 g, 2.9 eq), and bis(pinacolato)diboron (8.0 g, 8.1 eq) in 1,4-dioxane (20 mL). Sparge with $N_2$ for ten min. Add 1,1'-bis(diphenylphosphino)ferrocene-palladium(ii)dichloride dichloromethane complex (0.48 g, 0.15 eq). Heat at 100° C. overnight. Add bis(pinacolato)diboron (2.5 g, 2.5 eq) and 1,1'-bis(diphenylphosphino)ferrocene-palladium(ii)dichloride dichloromethane complex (0.48 g, 0.15 eq). Heat at 100° C. for eight hr. Cool to rt. Concentrate the reaction mixture in vacuo. Dilute with EtOAc. Filter through diatomaceous earth and a small pad of silica gel. Concentrate the filtrate in vacuo. Purify by normal phase chromatography, eluting with a 0-100% B in A gradient (A: hexanes, B: 10% MeOH in EtOAc), to give the title compound as a brown solid (0.41 g, 32%). MS (ES) m/z=331 (M+H).

Preparation 16

{2-[(tert-Butoxycarbonyl)amino]-7-fluoro-1,3-benzothiazol-4-yl}boronic acid

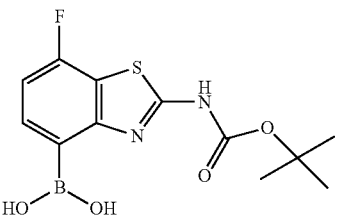 [SMILES: CC(C)(C)OC(=O)Nc1nc2c(B(O)O)ccc(F)c2s1]

Combine 2-[(tert-butoxycarbonyl)amino]-7-fluoro-1,3-benzothiazol-4-yl trifluoromethanesulfonate (20.0 g, 48.1 mmol), potassium acetate (14.2 g, 3.0 eq), bis(pinacolato)diboron (97.7 g, 8.0 eq), and tetrakis(triphenylphosphine)palladium(0) (5.55 g, 0.10 eq) in 1,4-dioxane (240 mL). Sparge with $N_2$ for ten min. Heat at 80° C. overnight. Cool to RT and dilute with water and EtOAc. Separate the layers. Dry the organic layer over anhydrous $MgSO_4$, filter, and concentrate the filtrate in vacuo. Add acetone (500 mL), water (500 mL), and $NH_4OAc$ (112 g, 30 eq). Add $NaIO_4$ (309 g, 30 eq), while maintaining the internal reaction temperature between 18-23° C. Stir vigorously at RT overnight. Dilute with EtOAc. Stir for 30 min, filter through diatomaceous earth, and separate the layers. Concentrate the organic layer in vacuo. Dilute the aqueous layer with saturated aqueous NaCl and extract twice with EtOAc. Combine the organic extracts with the previously concentrated organic layer. Wash numerous times, first with water, then saturated aqueous NaCl, then water and saturated aqueous $NaHCO_3$ (pH ~7). Dry the organic layer over anhydrous $MgSO_4$, filter, and concentrate the filtrate in vacuo. Slurry in hexanes with a small amount of DCM. Filter and wash the collected solid with hexanes to give the title compound as a tan solid (13.4 g, 89%). MS (ES) m/z=313 (M+H).

Preparation 17

{2-[(tert-Butoxycarbonyl)amino]-1,3-benzothiazol-4-yl}boronic acid

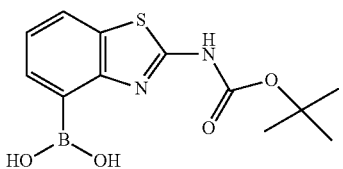 [SMILES: CC(C)(C)OC(=O)Nc1nc2c(B(O)O)cccc2s1]

Combine tert-butyl (4-bromo-1,3-benzothiazol-2-yl)carbamate (8.0 g, 24 mmol) and THF (115 mL). Place under $N_2$. Add NaH (60 mass % in paraffin oil, 1.5 g, 1.5 eq) in portions. Stir at RT for ten min, and then cool to −78° C. Add n-butyllithium (2.5 M in hexanes, 15 mL, 1.5 eq) dropwise. Stir for 25 min. Add triisopropyl borate (17 mL, 3.0 eq) dropwise. Stir for 25 min and then allow the reaction mixture to warm to RT. Quench with saturated aqueous $NH_4Cl$. Dilute with EtOAc, water, and saturated aqueous NaCl. Separate the layers. Dry the organic layer over anhydrous $MgSO_4$, filter, and concentrate the filtrate in vacuo.

Slurry in hexanes. Filter and wash the collected solid with hexanes. Partially concentrate the filtrate, dissolve in minimal EtOAc, add hexanes, filter, and wash with hexanes to give more solid. Repeat until no more solids are formed. Combine the solids to give the title compound (6.2 g, 87%). MS (ES) m/z=295 (M+H).

Preparation 18 tert-Butyl 4-(7-bromo-6-chloro-8-fluoroquinazolin-4-yl)piperazine-1-carboxylate

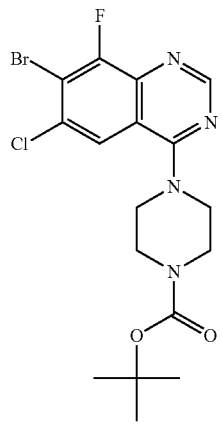 [SMILES: CC(C)(C)OC(=O)N1CCN(c2ncnc3c(F)c(Br)c(Cl)cc23)CC1]

Combine 7-bromo-4,6-dichloro-8-fluoroquinazoline (2.0 g, 6.9 mmol; see U.S. Pat. No. 9,840,516) and tert-butyl piperazine-1-carboxylate (3.8 g, 3.0 eq) in DCM (68 mL). Add TEA (9.6 mL, 10 eq). Stir at 35° C. under $N_2$ overnight. Concentrate the reaction mixture in vacuo. Dilute with EtOAc and water. Wash the organic layer with saturated aqueous NaCl. Dry the organic layer over anhydrous $MgSO_4$, filter, and concentrate the filtrate in vacuo. Dilute with DCM and hexanes, then filter. Concentrate the filtrate in vacuo. Purify by normal phase chromatography, eluting with a 0-5% MeOH in EtOAc gradient, to give the title compound (2.5 g, 80%). MS (ES) m/z=($^{79}$Br/$^{81}$Br) 445/447 (M+H).

Preparation 19 tert-Butyl 4-(7-bromo-6-chloroquinazolin-4-yl)piperazine-1-carboxalate

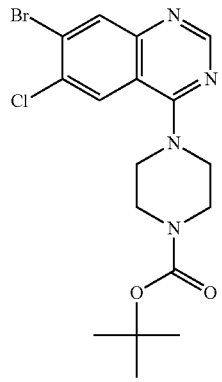 [SMILES: CC(C)(C)OC(=O)N1CCN(c2ncnc3cc(Br)c(Cl)cc23)CC1]

Combine 7-bromo-4,6-dichloroquinazoline (5.4 g, 16 mmol; see U.S. Pat. No. 9,840,516) and tert-butyl piperazine-1-carboxylate (3.3 g, 1.1 eq) in ACN (70 mL). Add $K_2CO_3$ (4.5 g, 2.0 eq). Stir at 60° C. for 4.5 hr. Cool to RT. Add water (200 mL) over 15 min. Filter and dry under vacuum to give the title compound as a white solid (6.8 g, 98%). MS (ES) m/z=($^{79}$Br/$^{81}$Br) 427/429 (M+H).

Preparation 20 tert-Butyl 4-(7-bromo-6,8-dichloroquinazolin-4-yl)piperazine-1-carboxylate

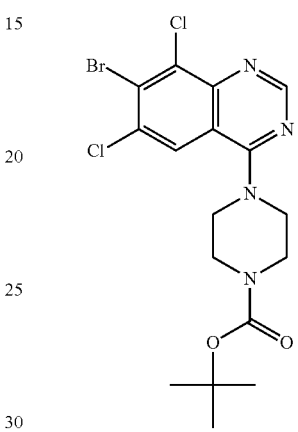

Prepare the title compound in a manner analogous to the method described in Preparation 19. MS (ES) m/z 463 (M+H)

Preparation 21 tert-Butyl 4-(7-{2-[(tert-butoxycarbonyl)amino]-7-fluoro-1,3-benzothiazol-4-yl}-6-chloro-8-fluoroquinazolin-4-yl)piperazine-1-carboxylate

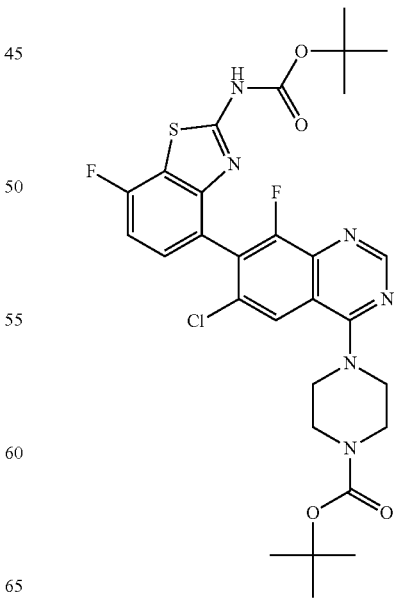

Combine tert-butyl 4-(7-bromo-6-chloro-8-fluoroquinazolin-4-yl)piperazine-1-carboxylate (0.60 g, 1.4 mmol), {2-[(tert-butoxycarbonyl)amino]-7-fluoro-1,3-benzothiazol-4-yl}boronic acid (0.47 g, 1.1 eq), and potassium phosphate (0.43 g, 1.5 eq) in 1,4-dioxane (10 mL) and water (3 mL). Sparge with $N_2$ for ten min. Add 1,1'-bis(di-tert-butylphosphino) ferrocene palladium dichloride (0.085 g, 0.10 eq). Stir at 90° C. for 105 min. Cool to RT. Dilute with water (1 mL) and filter through diatomaceous earth. Wash with EtOAc. Concentrate the filtrate in vacuo and purify by normal phase chromatography, eluting with 20% acetone in hexanes, to give the title compound as a white solid (0.85 g, 89%). MS (ES) m/z=633 (M+H).

Prepare the following compounds in Table 1 analogous to the method described in Preparation 21.

TABLE 1

| Prep # | Chemical Name | Structure | MS (ES) m/z (M + H) |
|---|---|---|---|
| 22 | tert-Butyl 4-(7-{2-[(tert-butoxycarbonyl)amino]-6,7-difluoro-1,3-benzothiazol-4-yl}-6-chloro-8-fluoroquinazolin-4-yl)piperazine-1-carboxylate | 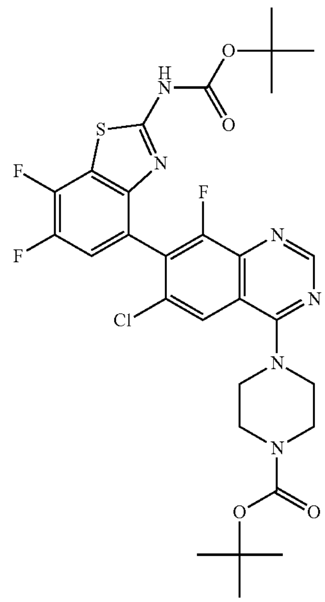 [SMILES: CC(C)(C)OC(=O)Nc1nc2c(-c3c(Cl)cc4c(N5CCN(C(=O)OC(C)(C)C)CC5)ncnc4c3F)cc(F)c(F)c2s1] | 651 |
| 23 | tert-Butyl 4-(7-{2-[(tert-butoxycarbonyl)amino]-7-fluoro-1,3-benzothiazol-4-yl}-6-chloroquinazolin-4-yl)piperazine-1-carboxylate | 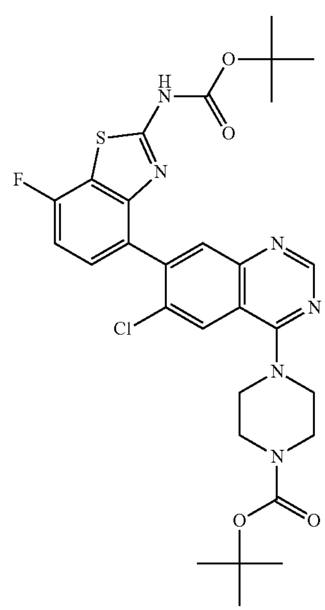 [SMILES: CC(C)(C)OC(=O)Nc1nc2c(-c3cc4ncnc(N5CCN(C(=O)OC(C)(C)C)CC5)c4cc3Cl)ccc(F)c2s1] | 615 |

TABLE 1-continued

| Prep # | Chemical Name | Structure | MS (ES) m/z (M + H) |
|---|---|---|---|
| 24 | tert-Butyl 4-(7-{2-[(tert-butoxycarbonyl)amino]-7-fluoro-1,3-benzothiazol-4-yl}-6,8-dichloroquinazolin-4-yl)piperazine-1-carboxylate | 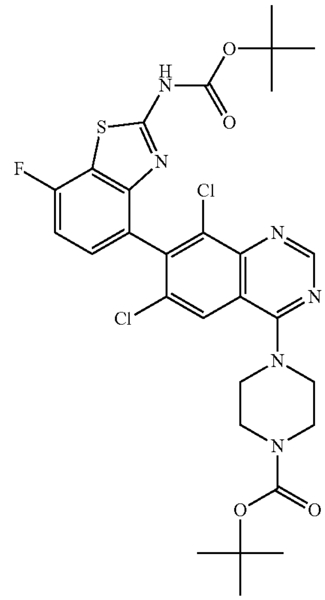 | 649 |
| 25 | tert-Butyl 4-(7-{2-[(tert-butoxycarbonyl)amino]-1,3-benzothiazol-4-yl}-6-chloro-8-fluoroquinazolin-4-yl)piperazine-1-carboxylate | 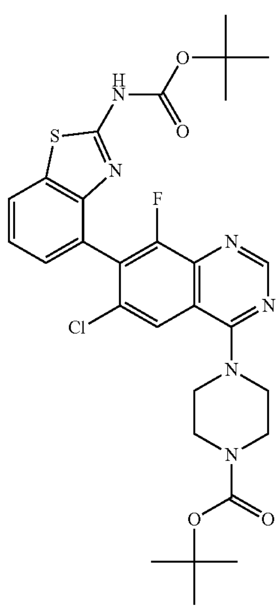 [SMILES: CC(C)(C)OC(=O)Nc1nc2c(-c3c(Cl)cc4c(N5CCN(C(=O)OC(C)(C)C)CC5)ncnc4c3F)cccc2s1] | 615 |

TABLE 1-continued

| Prep # | Chemical Name | Structure | MS (ES) m/z (M + H) |
|---|---|---|---|
| 26 | tert-Butyl 4-(7-{2-[(tert-butoxycarbonyl)amino]-5,7-difluoro-1,3-benzothiazol-4-yl}-6-chloro-8-fluoroquinazolin-4-yl)piperazine-1-carboxylate | 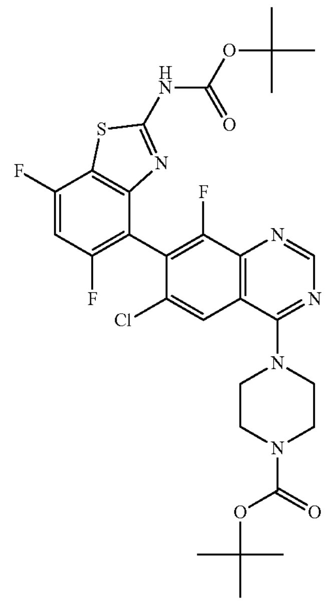 [SMILES: CC(C)(C)OC(=O)Nc1nc2c(-c3c(Cl)cc4c(N5CCN(C(=O)OC(C)(C)C)CC5)ncnc4c3F)c(F)cc(F)c2s1] | 651 |

Preparation 27

KRas Probe

N-(2-{2-[2-({6-Chloro-8-fluoro-7-(3-hydroxynaphthalen-1-yl)-4-[4-(prop-2-enoyl)piperazin-1-yl]quinazolin-2-yl}amino)ethoxy]ethoxy}ethyl)-5-[(3aS,4S,6aR)-2-oxohexahydro-1H-thieno[3,4-d]imidazol-4-yl]pentanamide

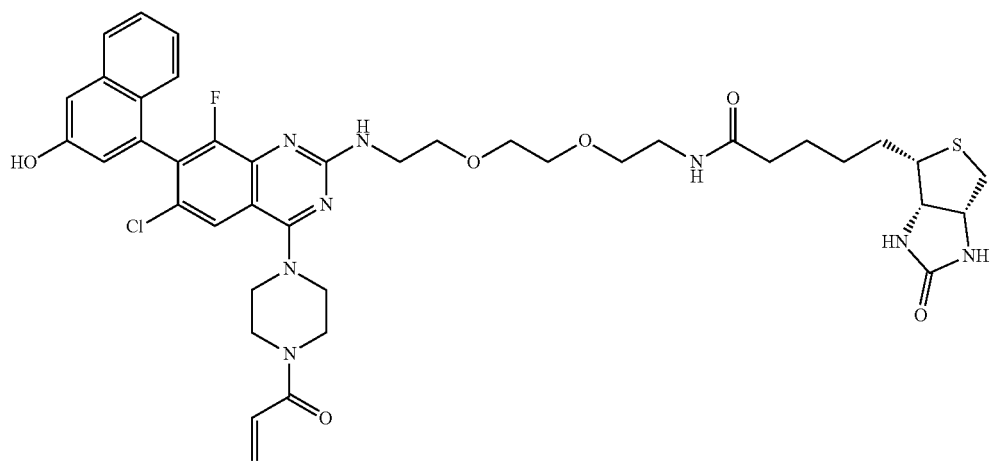 [SMILES: C=CC(=O)N1CCN(c2nc(NCCOCCOCCNC(=O)CCCC[C@@H]3SC[C@@H]4NC(=O)N[C@@H]43)nc3c(F)c(-c4cc(O)cc5ccccc45)c(Cl)cc23)CC1]

Step A: Combine tert-butyl 4-(7-bromo-2,6-dichloro-8-fluoroquinazolin-4-yl)piperazine-1-carboxylate (0.51 g, 1.1 mmol) and IPA (5 mL). Add DIPEA (0.55 mL, 3.0 eq) and 5-[(3aS,4S,6aR)-2-oxohexahydro-1H-thieno[3,4-d]imidazol-4-yl]-N-[2-[2-(2-aminoethoxy)ethoxy]ethyl]pentanamide (0.48 g, 1.2 eq). Heat to 120° C. in a microwave reactor for six hr. Cool to RT. Dilute with saturated aqueous $NH_4Cl$ and 25% IPA in $CHCl_3$. Separate the layers. Wash the organic layer with saturated aqueous NaCl. Dry the organic layer over anhydrous $Na_2SO_4$, filter, and concentrate the filtrate in vacuo. Purify by normal phase chromatography, eluting with a 50-100% B in A gradient (A: hexanes, B: 10% MeOH in DCM), to give the tert-butyl 4-{7-bromo-6-chloro-8-fluoro-2-[(2-{2-[2-({5-[(3aS,4S,6aR)-2-oxohexahydro-1H-thieno[3,4-d]imidazol-4-yl]pentanoyl}amino) ethoxy]ethoxy}ethyl)amino]quinazolin-4-yl}piperazine-1-carboxylate as a yellow solid (0.68 g, 78%). MS (ES) m/z=819 (M+H).

Step B: Combine tert-butyl 4-{7-bromo-6-chloro-8-fluoro-2-[(2-{2-[2-({5-[(3aS,4S,6aR)-2-oxohexahydro-1H-thieno[3,4-d]imidazol-4-yl]pentanoyl}amino)ethoxy]ethoxy}ethyl)amino]quinazolin-4-yl}piperazine-1-carboxylate (0.30 g, 0.37 mmol), 1,4-dioxane (4 mL), and water (0.75 mL). Add $K_2CO_3$ (0.24 g, 3.0 eq), 4-(4,4,5,5-tetramethyl-1,3,2-dioxaborolan-2-yl)naphthalen-2-ol (0.20 g, 2.0 eq), and tetrakis(triphenylphosphine) palladium(0) (0.085 g, 0.20 eq). Stir at 85° C. under $N_2$ for 12 hrs. Cool to RT. Filter to remove solids. Dilute the filtrate with saturated aqueous $NH_4Cl$ and EtOAc. Separate the layers. Wash the organic layer with saturated aqueous NaCl. Dry the organic layer over anhydrous $Na_2SO_4$, filter, and concentrate the filtrate in vacuo. Purify by normal phase chromatography, eluting with a 90-100% B in A gradient (A: hexanes, B: 10% MeOH in DCM), to give tert-butyl 4-{6-chloro-8-fluoro-7-(3-hydroxynaphthalen-1-yl)-2-[(2-{2-[2-({5-[(3aS,4S,6aR)-2-oxohexahydro-1H-thieno[3,4-d]imidazol-4-yl]pentanoyl} amino) ethoxy]ethoxy}ethyl)amino]quinazolin-4-yl}piperazine-1-carboxylate as a yellow solid (0.31 g, 96%). MS (ES) m/z=881 (M+H).

Step C: Cool a solution of tert-butyl 4-{6-chloro-8-fluoro-7-(3-hydroxynaphthalen-1-yl)-2-[(2-{2-[2-({5-[(3aS,4S,6aR)-2-oxohexahydro-1H-thieno[3,4-d]imidazol-4-yl]pentanoyl}amino)ethoxy]ethoxy}ethyl)amino]quinazolin-4-yl}piperazine-1-carboxylate (0.31 g, 0.35 mmol) in MeOH (4 mL) to 0° C. Add HCl (3 M in MeOH, 6 mL, 50 eq) and stir at 0° C. for 30 min. Warm to RT and stir overnight. Concentrate the reaction mixture in vacuo. Dilute with DCM and concentrate in vacuo. Dilute with hexanes and stir at RT for two hrs. Filter and dry the resulting solid under vacuum to give N-{2-[2-(2-{[6-chloro-8-fluoro-7-(3-hydroxynaphthalen-1-yl)-4-(piperazin-1-yl)quinazolin-2-yl]amino}ethoxy) ethoxy]ethyl}-5-[(3aS,4S,6aR)-2-oxohexahydro-1H-thieno[3,4-d]imidazol-4-yl]pentanamide hydrogen chloride. Neutralize this hydrochloride salt (0.19 g, 0.23 mmol) by combining with DIPEA (0.16 mL, 4.0 eq) in DCM (2.5 mL). Cool to −78° C. Add acryloyl chloride (0.5 M in DCM, 0.4 mL, 0.9 eq). After 30 min, warm to RT. After one hr, dilute with MeOH (1 mL) and concentrate the reaction mixture in vacuo. Purify by reverse phase chromatography, eluting with a 35-60% B in A gradient (A: 10 mM aqueous $NH_4HCO_3$ with 5% MeOH; B: ACN), to give the title compound as a white solid (0.027 g, 14%). MS (ES) m/z=835 (M+H).

Example 1

1-{4-[7-(2-Amino-7-fluoro-1,3-benzothiazol-4-yl)-6-chloro-8-fluoroquinazolin-4-yl]piperazin-1-yl}prop-2-en-1-one

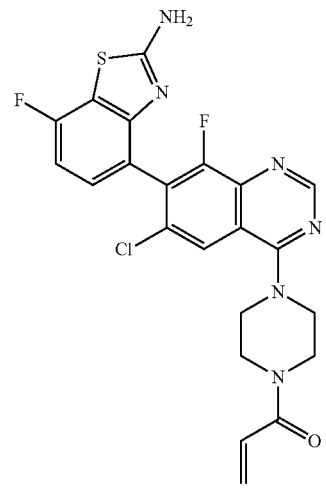 [SMILES: C=CC(=O)N1CCN(c2ncnc3c(F)c(-c4ccc(F)c5sc(N)nc45)c(Cl)cc23)CC1]

Add TFA (2 mL) to a solution of tert-butyl 4-(7-{2-[(tert-butoxycarbonyl)amino]-7-fluoro-1,3-benzothiazol-4-yl}-6-chloro-8-fluoroquinazolin-4-yl)piperazine-1-carboxylate (0.76 g, 1.2 mmol) in DCM (10 mL). Stir at RT for three days. Concentrate the reaction mixture in vacuo. Dilute with DCM and concentrate in vacuo; repeat three times. Dilute with $Et_2O$ (30 mL) and stir rapidly at RT for three hrs. Filter and dry under vacuum to give 4-[6-chloro-8-fluoro-4-(piperazin-1-yl)quinazolin-7-yl]-7-fluoro-1,3-benzothiazol-2-amine ditrifluoroacetic acid.

Combine 4-[6-chloro-8-fluoro-4-(piperazin-1-yl)quinazolin-7-yl]-7-fluoro-1,3-benzothiazol-2-amine ditrifluoroacetic acid (0.50 g, 0.91 mmol) and potassium carbonate (0.56 g, 4.4 eq) in 2-methyltetrahydrofuran (5 mL) and water (5 mL). Cool to 0° C. Add acryloyl chloride (0.5 M in 2-methyltetrahydrofuran, 2.0 mL, 1.1 eq). After five min, dilute with EtOAc and water. Separate the layers. Wash the organic layer with saturated aqueous NaCl. Dry the organic layer over anhydrous $Na_2SO_4$, filter, and concentrate the filtrate in vacuo. Dissolve the residue in DCM (5 mL). Stir rapidly and add hexanes (15 mL) slowly. Stir at RT for 15 min, filter, and dry the collected solid under vacuum to give the title compound as a white solid (0.32 g, 72%). MS (ES) m/z=487 (M+H).

Prepare the following Examples in Table 2 analogous to the method described in Example 1 using the appropriate Preparation 22-26 described above.

TABLE 2

| Ex # | Chemical Name | Structure | MS (ES) m/z (M + H) | Yield |
|---|---|---|---|---|
| 2 | 1-{4-[7-(2-Amino-7-fluoro-1,3-benzothiazol-4-yl)-6,8-dichloroquinazolin-4-yl]piperazin-1-yl}prop-2-en-1-one | 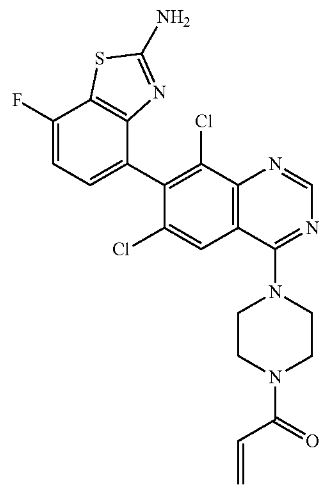 | 503 | 66% |
| 3 | 1-{4-[7-(2-Amino-6,7-difluoro-1,3-benzothiazol-4-yl)-6-chloro-8-fluoroquinazolin-4-yl]piperazin-1-yl}prop-2-en-1-one | 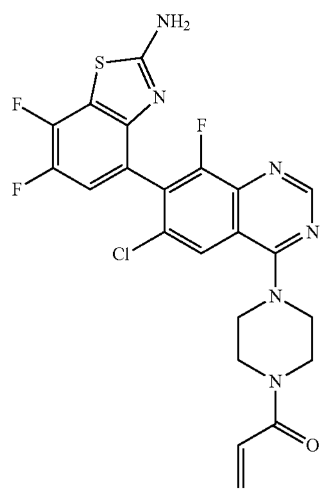 [SMILES: C=CC(=O)N1CCN(c2ncnc3c(F)c(-c4cc(F)c(F)c5sc(N)nc45)c(Cl)cc23)CC1] | 505 | 70% |
| 4 | 1-{4-[7-(2-Amino-7-fluoro-1,3-benzothiazol-4-yl)-6-chloroquinazolin-4-yl]piperazin-1-yl}prop-2-en-1-one | 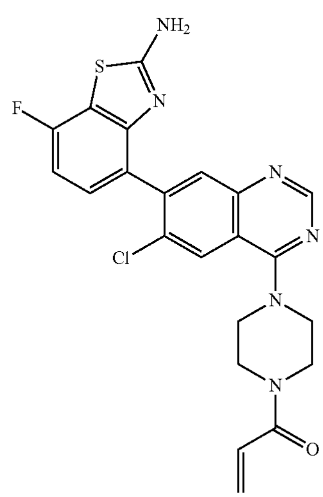 [SMILES: C=CC(=O)N1CCN(c2ncnc3cc(-c4ccc(F)c5sc(N)nc45)c(Cl)cc23)CC1] | 469 | 15% |

TABLE 2-continued

| Ex # | Chemical Name | Structure | MS (ES) m/z (M + H) | Yield |
|---|---|---|---|---|
| 5 | 1-{4-[7-(2-Amino-1,3-benzothiazol-4-yl)-6-chloro-8-fluoroquinazolin-4-yl]piperazin-1-yl}prop-2-en-1-one | 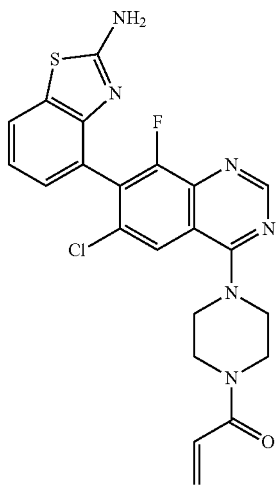 [SMILES: C=CC(=O)N1CCN(c2ncnc3c(F)c(-c4cccc5sc(N)nc45)c(Cl)cc23)CC1] | 469 | 86% |
| 6A‡ | 1-{4-[7-(2-Amino-5,7-difluoro-1,3-benzothiazol-4-yl)-6-chloro-8-fluoroquinazolin-4-yl]piperazin-1-yl}prop-2-en-1-one Atropisomer 1 | 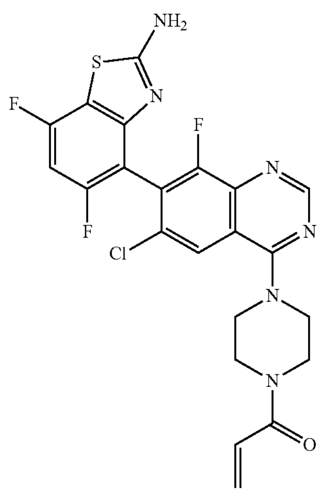 [SMILES: C=CC(=O)N1CCN(c2ncnc3c(F)c(-c4c(F)cc(F)c5sc(N)nc45)c(Cl)cc23)CC1] | 505 | 23% |
| 6B‡ | 1-{4-[7-(2-Amino-5,7-difluoro-1,3-benzothiazol-4-yl)-6-chloro-8-fluoroquinazolin-4-yl]piperazin-1-yl}prop-2-en-1-one Atropisomer 2 | 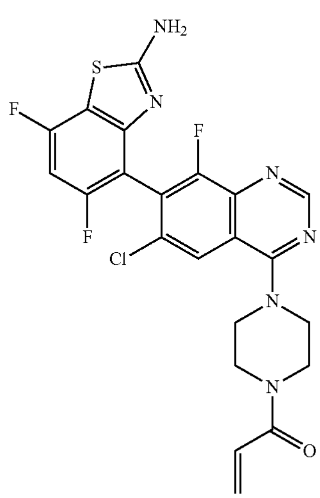 [SMILES: C=CC(=O)N1CCN(c2ncnc3c(F)c(-c4c(F)cc(F)c5sc(N)nc45)c(Cl)cc23)CC1] | 505 | 23% |

‡Separate 1-{4-[7-(2-amino-5,7-difluoro-1,3-benzothiazol-4-yl)-6-chloro-8-fluoroquinazolin-4-yl]piperazin-1-yl}prop-2-en-1-one (0.062 g) with the following chiral chromatography conditions to give the title compounds (0.025 g and 0.025 g): Atropisomer 1 >99% ee, 40% EtOH/60% CO₂, 80 mL/min, 21 × 250 mm, Chiralcel ® OD-H. MS (ES) m/z = 505 (M + H). Atropisomer 2 >99% ee, 40% EtOH/60% CO₂, 80 mL/min, 21 × 250 mm, Chiralcel ® OD-H. MS (ES) m/z = 505 (M + H). The structures of the two atropisomers of Example 6, are illustrated below.

Example 7

1-{4-[7-(2-Amino-7-fluoro-1,3-benzothiazol-4-yl)-6-chloro-8-fluoroquinazolin-4-yl]piperazin-1-yl}prop-2-en-1-one; hemi-malonate salt

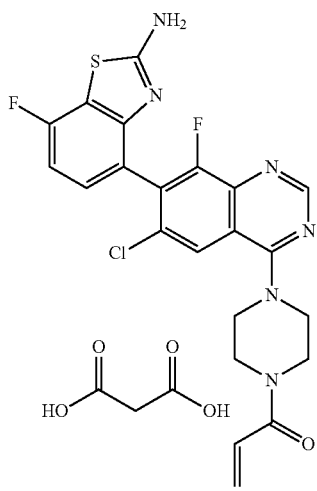

Add 9:1 THF:water (2.2 mL) to a vial containing 1-{4-[7-(2-amino-7-fluoro-1,3-benzothiazol-4-yl)-6-chloro-8-fluoroquinazolin-4-yl]piperazin-1-yl}prop-2-en-1-one (199 mg, 0.409 mmol) to give a yellow solution. In a separate vial, add THF (0.1 mL) to malonic acid (48 mg, 1.1 eq) to obtain a colorless solution. Add the malonic acid solution to the Example 1 solution and rinse with 0.1 mL THF. Add EtOAc (5 mL) portionwise with periodic seeding to give a hazy mixture. Concentrate the mixture partially in vacuo to remove solvent. Remove about 5.4 g of total mass via concentration, to form a suspension. Stir the mixture at RT to give a thick suspension. Add EtOAc (1.5 mL) to thin out the suspension and then filter and rinse with EtOAc (5 mL) to rinse all of the solids from the vial. The solids are dried in a vacuum oven at 50° C. to give the title compound as a pale yellow solid (177 mg, 79%). $^1$H NMR (DMSO-$d_6$): δ12.64 (br s, 1H), 8.68 (s, 1H), 8.00 (d, J=1.4 Hz, 1H), 7.92 (br s, 2H), 7.25 (dd, J=8.4, 5.7 Hz, 1H), 7.06 (dd, J=9.1, 8.6 Hz, 1H), 6.81 (dd, J=16.8, 10.5 Hz, 1H), 6.16 (dd, J=16.8, 2.4 Hz, 1H), 5.73 (dd, J=10.5, 2.4 Hz, 1H), 3.86-3.96 (m, 4H), 3.82 (br s, 2H), 3.75 (br s, 2H), 3.22 (s, 1H). Seed crystal prep: Add 9:1 THF:water (5 mL) to 1-{4-[7-(2-amino-7-fluoro-1,3-benzothiazol-4-yl)-6-chloro-8-fluoroquinazolin-4-yl]piperazin-1-yl}prop-2-en-1-one (149 mg, 0.306 mmol) followed by malonic acid (50 mg, 1.55 eq). Dried solution under $N_2$ for 48 hrs. Add EtOAc (5 mL) to the resulting oil and stir at 50° C. for 2 hrs to form a slurry of white solid. Filtered to give 1-{4-[7-(2-amino-7-fluoro-1,3-benzothiazol-4-yl)-6-chloro-8-fluoroquinazolin-4-yl]piperazin-1-yl}prop-2-en-1-one; hemi-malonate crystals for seeding.

Example 8

1-{4-[7-(2-Amino-7-fluoro-1,3-benzothiazol-4-yl)-6-chloro-8-fluoroquinazolin-4-yl]piperazin-1-yl}prop-2-en-1-one; mesylate salt

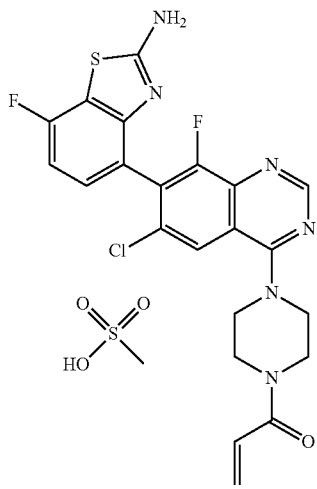

Add 1-{4-[7-(2-amino-7-fluoro-1,3-benzothiazol-4-yl)-6-chloro-8-fluoroquinazolin-4-yl]piperazin-1-yl}prop-2-en-1-one (6.56 g, 13.5 mmol) to a flask. Add 9:1 THF:water (55 mL) and heat the mixture to 50° C. Filter the resulting solution and rinse with 9:1 THF:water (3.3 mL). Charge the filtered solution to a syringe, and place into a syringe pump. Separately, add methanesulfonic acid (0.83 mL, 0.95 eq) to THF (13 mL). Charge this solution to a syringe and place into a second syringe pump. Add 1-{4-[7-(2-Amino-7-fluoro-1,3-benzothiazol-4-yl)-6-chloro-8-fluoroquinazolin-4-yl]piperazin-1-yl}prop-2-en-1-one mesylate seeds (65 mg) to a flask, along with THF (13 mL). Stir the seed slurry at rt. Add the 1-{4-[7-(2-amino-7-fluoro-1,3-benzothiazol-4-yl)-6-chloro-8-fluoroquinazolin-4-yl]piperazin-1-yl}prop-2-en-1-one solution and methanesulfonic acid solution to the seed slurry, starting with 0.225 mL/min of the 1-{4-[7-(2-amino-7-fluoro-1,3-benzothiazol-4-yl)-6-chloro-8-fluoroquinazolin-4-yl]piperazin-1-yl}prop-2-en-1-one solution and 0.0575 mL/min of the methanesulfonic acid solution. After 1 hr, increase the addition rates to 0.3 mL/min and 0.077 mL/min, respectively. After another 1 hr, increase the addition rates to 0.45 mL/min and 0.115 mL/min, respectively. After the co-addition is complete, stir the slurry for about 45 min. Filter the slurry and rinse with 95:5 THF:water (2×13 mL). Dry the wetcake under vacuum at 50° C. to a constant weight. Isolate the title compound as a white solid (6.22 g, 79%). $^1$H NMR (400 MHz, DMSO-$d_6$, 25° C.): δ=8.82 (s, 1H), 8.17 (d, J=1.2 Hz, 1H), 7.98 (br s, 2H), 7.29 (dd, J=8.5, 5.7 Hz, 1H), 7.11 (t, J=8.8 Hz, 1H), 6.82 (dd, J=16.7, 10.4 Hz, 1H), 6.19 (dd, J=16.7, 2.4 Hz, 1H), 5.76 (dd, J=10.4, 2.4 Hz, 1H), 4.12-4.25 (m, 4H), 3.90 (br s, 2H), 3.81 (br s, 2H), 2.35 ppm (s, 3H). Seed crystal prep: Heat a mixture of 1-{4-[7-(2-amino-7-fluoro-1,3-benzothiazol-4-yl)-6-chloro-8-fluoroquinazolin-4-yl]piperazin-1-yl}prop-2-en-1-one (218 mg, 0.448 mmol) in THF (3 mL) at 60° C.

Add methanesulfonic acid (40 μL) diluted in THF (2 mL) to the mixture. Add THF (10 mL) to the resulting slurry and stir at RT. Filter and dry the collected solids under nitrogen for 15 min to give the 1-{4-[7-(2-Amino-7-fluoro-1,3-benzothiazol-4-yl)-6-chloro-8-fluoroquinazolin-4-yl]piperazin-1-yl}prop-2-en-1-one; mesylate crystals for seeding.

Example 9

X-Ray Powder Diffraction (XRPD) of Crystalline Forms

Obtain the XRPD patterns of crystalline solids on a Bruker D4 Endeavor X-ray powder diffractometer, equipped with a CuKα source and a Vantec detector, operating at 35 kV and 50 mA. Scan the sample between 4 and 40 2θ°, with a step size of 0.008 2θ° and a scan rate of 0.5 seconds/step, and using 1.0 mm divergence, 6.6 mm fixed anti-scatter, and 11.3 mm detector slits. Pack the dry powder on a quartz sample holder and a smooth surface is obtained using a glass slide. Collect the crystal form diffraction patterns at rt and relative humidity. Determine crystal peak positions in MDI-Jade after whole pattern shifting based on an internal NIST 675 standard with peaks at 8.853 and 26.774 2θ°. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g. The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature at which a sample is analyzed, sample displacement, or the presence or absence of an internal standard. In the present case, a peak position variability of ±0.2 2θ° is presumed to take into account these potential variations without hindering the unequivocal identification of the indicated crystal form. Confirmation of a crystal form may be made based on any unique combination of distinguishing peaks.

Example 9a

XRPD of 1-{4-[7-(2-Amino-7-fluoro-1,3-benzothiazol-4-yl)-6-chloro-8-fluoroquinazolin-4-yl]piperazin-1-yl}prop-2-en-1-one; hemi-malonate salt A prepared sample of the crystalline hemi-malonate form is characterized by an XRPD pattern using CuKα radiation as having diffraction peaks (2-theta values) as described in Table 3 below, and in particular having peaks at 5.4° in combination with one or more of the peaks selected from the group consisting of 13.5°, 7.1°, and 23.0°; with a tolerance for the diffraction angles of 0.2 degrees.

TABLE 3

XRPD peaks of the crystalline hemi-malonate of Example 1.

| Peak | Angle +/- 0.2 (2θ°) | Relative Intensity (% of most intense peak) |
|---|---|---|
| 1 | 5.4 | 100.00 |
| 2 | 6.4 | 22.00 |
| 3 | 7.1 | 49.10 |
| 4 | 11.1 | 34.50 |
| 5 | 13.5 | 66.20 |
| 6 | 15.2 | 28.60 |
| 7 | 17.1 | 23.20 |
| 8 | 20.7 | 26.50 |
| 9 | 21.2 | 24.80 |
| 10 | 23.0 | 39.80 |

Example 9b

XRPD of 1-{4-[7-(2-Amino-7-fluoro-1,3-benzothiazol-4-yl)-6-chloro-8-fluoroquinazolin-4-yl]piperazin-1-yl}prop-2-en-1-one; mesylate salt A prepared sample of the crystalline mesylate salt is characterized by an XRPD pattern using CuKα radiation as having diffraction peaks (2-theta values) as described in Table 4 below, and in particular having peaks at 6.1° in combination with one or more of the peaks selected from the group consisting of 21.3°, 18.6°, and 19.8°; with a tolerance for the diffraction angles of 0.2 degrees.

TABLE 4

XRPD peaks of the crystalline mesylate salt of Example 1

| Peak | Angle +/- 0.2 (2θ°) | Relative Intensity (% of most intense peak) |
|---|---|---|
| 1 | 6.1 | 100.00 |
| 2 | 13.2 | 22.10 |
| 3 | 14.2 | 17.70 |
| 4 | 18.6 | 24.30 |
| 5 | 19.8 | 24.20 |
| 6 | 20.3 | 20.90 |
| 7 | 21.3 | 42.10 |
| 8 | 23.9 | 18.30 |
| 9 | 24.6 | 19.60 |
| 10 | 25.4 | 21.90 |

Biological Assays

KRas G12C Probe Occupancy TR-FRET Assay

This assay measures the ability of an inhibitor to compete with a probe for binding to and covalently modifying KRas G12C at codon 12. The signal is generated by the time-resolved transfer of fluorescence between europium on an antibody bound to KRas G12C Europium-labeled Anti-Histidine Tag Antibody LanthaScreen (the Eu Anti-His antibody) and fluorescent Tracer 647 (Alexa Fluor™) bound to KRas G12C through streptavidin and a biotinylated inhibitor (the "KRas Probe", see Preparation 27).

Inhibitors are tested in dose response format from 10 mM stocks in 100% DMSO. The Labycyte Echo® 555 is used to dilute and transfer 100 nL per well containing a 10 point, 2.8-fold serial dilution to an assay plate. Two copies of the assay plate are prepared to measure the potency after a 5 and 60 min incubation of the inhibitor with KRas G12C. His-tagged KRas G12C (20 nM) is added to the plates in assay buffer (20 mM Tris-HCl, pH 7.5, 0.01% TX-100, and 1 mM DTT). After a 5 or 60 min incubation, 1 μM KRas Probe is added and allowed to covalently modify free KRas G12C for 1 hour. This is diluted 4-fold in buffer containing Eu Anti-His antibody and Streptavidin-Coated Tracer 647 (both from Life Technologies) to achieve KRas G12C (5 nM), Anti-His Antibody (2 nM), KRas Probe (300 nM), and Streptavidin Coated Tracer 647 (500 nM). After 30 min, the fluorescent signal is read on an Envision™ Plate Reader (excitation at 340 nM, tracer emission at 665 nM, and antibody emission at 615 nM). Maximum control wells lack inhibitor and minimum control wells lack both inhibitor and KRas G12C. The signal ratio (em at 665/em at 615) is converted to percent inhibition using the following equation: % Inhibition=100−[(Test Compound Signal−Median Minimum Signal)/(Median Maximum Signal−Median Minimum Signal)×100]. The $IC_{50}$ is determined by fitting the percent inhibition at each inhibitor concentration to the four parameter nonlinear logistic equation using Genedata Screener®: $y=(A+((B-A)/(1+((C/x)^D))))$ where, y=% inhibition, A=minimum asymptote, B=maximum asymptote, C=relative $IC_{50}$ or the inhibitor concentration producing 50% inhibition within the fitted range of both asymptotes, and D=Hill Slope.

Compounds within the scope of this invention are evaluated in this assay substantially as described above. Exemplified compounds of the invention evaluated in this assay exhibit an $IC_{50}$ of less than 500 nM for 60 min incubation and less than 1200 nM for 5 min incubation. The compound of Example 1 evaluated in this assay exhibits an $IC_{50}$ of 0.025 and 0.024 μm, respectively at 5 and 60 min, n=5. This data show that the compounds of the Examples exhibit KRas G12C inhibition activity in this binding assay as described in Table 5.

TABLE 5

| Compound | TR-FRET 60 min (uM) | pERK (uM) | RAS-GTP (uM) |
| --- | --- | --- | --- |
| Example 1 | 0.024 (n = 4) | 0.00566 (n = 13) | 0.0371 (n = 10) |
| Example 2 | 0.0476 (n = 4) | 0.0194 (n = 5) | 0.148 (n = 5) |
| Example 3 | 0.0209 (n = 4) | 0.0153 (n = 7) | 0.166 (n = 8) |
| Example 4 | 0.0250 (n = 4) | 0.0271 (n = 5) | 0.234 (n = 5) |
| Example 5 | 0.0278 (n = 2) | 0.00973 (n = 6) | 0.104 (n = 5) |
| Example 6a | <0.0189 (n = 2) | 0.00394 (n = 2) | 0.0117 (n = 3) |
| Example 6b | 0.449 (n = 1) | 0.256 (n = 2) | 0.743 (n = 3) |
| [structure] | 0.578 (n = 3) | 1.60 (n = 2) | 3.78 (n = 2) |
| [structure] | 0.0452 (n = 201) | 0.204 (n = 6) | 0.392 (n = 199) |
| [structure] | 82.2 (n = 4) | >5.00 (n = 4) | >50.0 (n = 4) |

Comparitor compounds found in WO2015/0545572.

The above data demonstrates that Example 1 has an unexpected improvement in potency as compared against certain KRas G12C inhibitors in the art.

H358 Cellular Phospho-ERK AlphaLISA®

This assay is used to measure the ability of test compounds to inhibit the phosphorylation of p-ERK1/2, a downstream effector of KRas in Human lung cancer cells H358 (ATCC CRL-5807). Briefly, the AlphaLISA® SureFire® Ultra™ p-ERK 1/2 (Thr202/Tyr204) assay is a sandwich immunoassay for quantitative detection of phospho-ERK 1/2 (phosphorylated on Thr202/Tyr204 in ERK1, or Thr185/Tyr187 in ERK2) in cellular lysates using Alpha Technology (Perkin Elmer Cat #ALSU-PERK-A50K).

H358 cells are plated at 40K cells per well in 100 µL media (RPMI 1640, GIBCO Cat #22400-071) containing 10% FBS (GIBCO Cat #: 10082-147) in a 96 well plate (Costar #3596) and are incubated overnight in humid trays at 37° C., 5% $CO_2$. The next morning, 10 µL of serially-diluted (3-fold) test compounds (50 µM top concentration) and 10 uL of controls (Maximum signal wells: 5% DMSO and Minimum signal wells: 2 µM of N-(3-{3-cyclopropyl-5-[(2-fluoro-4-iodophenyl)amino]-6,8-dimethyl-2,4,7-trioxo-3,4,6,7-tetrahydropyrido[4,3-D]pyrimidin-1(2H)-yl}phenyl)acetamide (trametinib, as a positive control) are added to the cell plate and incubated for 2 hr in humid trays at 37° C./5% $CO_2$. Lysis Buffer is prepared at RT containing a protease and phosphatase inhibitor cocktail. Culture medium is removed by inverting and shaking the cell plate in the sink and then blotting onto a paper towel. Lysis buffer is added to the cell plate (50 µL per well) and the plate is incubated at RT for 10 min on a shaker. For p-ERK detection, acceptor beads are diluted into a suspension mixture with buffer. Using a Starlett liquid handler, 5 µL of acceptor beads and 2 µL of cell lysate are transferred as a single-step in-tip dilution to a 384 well assay plate. The assay plate is sealed with foil and is incubated at RT for 2 hrs. Donor beads are diluted into a suspension mixture with buffer. Using the Starlet, 5 µL of donor beads are added to the assay plate that is then sealed, wrapped with foil. The plate is incubated at RT for 2 hrs in the dark. The assay plate is then read on an EnVision™ Plate Reader (Perkin Elmer) using a luminescence program.

The signal is converted to percent inhibition using the following equation: % Inhibition=100−[(Test Compound Signal−Median Minimum Signal)/(Median Maximum Signal−Median Min Signal)×100]. The Maximum signal is a control well without inhibitor. The Minimum signal is a control well containing a reference inhibitor sufficient to fully inhibit activity. The $IC_{50}$ is determined by fitting the percent inhibition at each inhibitor concentration to the four parameter nonlinear logistic equation using Genedata Screener®: $y=(A+((B-A)/(1+((C/x)^D))))$ where, y=% inhibition, A=minimum asymptote, B=maximum asymptote, C=relative $IC_{50}$ or the inhibitor concentration producing 50% inhibition within the fitted range of both asymptotes, and D=Hill Slope.

Compounds within the scope of this invention are evaluated in this assay substantially as described above. The compounds of the Examples exhibited a relative $IC_{50}$ of less than 0.300 µM. The compound of Example 1 exhibited a relative $IC_{50}$ in this assay of 0.0057 µM n=13. This data show that the compounds of the Examples exhibit KRas G12C inhibition activity in this cellular assay.

H358 Cellular Active RAS GTPase ELISA

This assay is used to measure the ability of test compounds to inhibit constitutive RAS GTPAse activity in human lung cancer cells H358 (ATCC CRL-5807). The RAS GTPase ELISA kit (Active Motif Cat #52097) contains a 96-well plate pre-coated with glutathione in order to capture a kit-supplied GST-Raf-RBD protein. Activated RAS (GTP-bound) in cell extracts specifically bind to the Raf-RBD. Bound RAS is detected with a primary antibody that recognizes human KRas. A secondary antibody conjugated with HRP recognizes the primary antibody and a development solution provides a chemiluminescent readout.

H358 cells are plated at 80,000 cells/well in 90 µL serum free media (RPMI 1640, GIBCO) and incubated overnight at 37° C./5% $CO_2$. The next morning, 10 µL of serially-diluted (3-fold) test compounds (500 µM top concentration) and 10 µL of controls (Maximum signal wells: 5% DMSO and Minimum signal wells: 500 µM LSN3429410 as an inhibitor) are added to the cell plate and incubated for 2 hr at 37° C./5% $CO_2$. Complete Lysis/Binding Buffer is prepared containing Protease Inhibitor cocktail and GST-Raf-RBD and stored on ice. One hour before cell plate incubation is completed, 50 µL of GST-Raf-RBD is diluted in lysis/binding buffer, and buffer is added to the ELISA assay plate and which is incubated for 1 hour at 4° C. with gently rocking. After 2 hr, the cells are washed with 100 µL ice-cold PBS and lysed with 100 µL lysis/binding buffer. The cell plate is shaken for 10 min at RT. The cell plate is then centrifuged at 1500 rpm for 10 min at RT. During this time, 1× Wash Buffer is prepared at RT and then is used to wash (3×100 µL) the GST-Raf-RBD coated assay plate. After washing, 50 µL of cell lysate is added to the GST-Raf-RBD coated assay plate and incubated for 1 hour at RT with gentle shaking. During this incubation period, 1× Antibody Binding Buffer is prepared and brought to RT. The assay plate is washed 3×100 µL with 1× Wash Buffer and then 50 µL of Primary Antibody (diluted 1:500 in 1× Antibody Binding buffer) is added. The plate is incubated for 1 hour at RT. The assay plate is washed 3×100 µl with 1× Wash Buffer and then 50 µL of Secondary Antibody (diluted 1:5000 in 1× Antibody Binding buffer) is added and incubated for 1 hour at RT. The assay plate is washed 4×100 µL with 1× Wash buffer and then 50 µL of chemiluminescent working solution is added at RT. The assay plate is then read on an EnVision™ Plate Reader (Perkin Elmer) using a luminescence program.

The signal is converted to percent inhibition using the following equation: % Inhibition=100−[(Test Compound Signal−Median Minimum Signal)/(Median Maximum Signal−Median Minimum Signal)×100]. The Maximum signal is a control well without inhibitor. The Minimum signal is a control well containing a reference inhibitor sufficient to fully inhibit activity. The $IC_{50}$ is determined by fitting the percent inhibition at each inhibitor concentration to the four parameter nonlinear logistic equation using Genedata Screener®: $y=(A+((B-A)/(1+((C/x)^D))))$ where, y=% inhibition, A=minimum asymptote, B=maximum asymptote, C=relative $IC_{50}$ or the inhibitor concentration producing 50% inhibition within the fitted range of both asymptotes, and D=Hill Slope.

Compounds within the scope of this invention are evaluated in this assay substantially as described above. The compounds of the Examples exhibited a relative $IC_{50}$ of less than 0.750 µM. The compound of Example 1 exhibited a relative IC$_{50}$ of 0.037 µM, n=10 in this assay. This data show that the compounds of the Examples exhibit KRas-GTP inhibition activity in this human lung cancer cell culture.

3D H358 Cell Proliferation Assay

Human lung cancer cells, H358, (ATCC CRL-5807) are used to evaluate compound inhibition in a 3D proliferation assay. Signal reflecting cell proliferation is detected with the CellTiterGlo® 3D reagent (Promega G9683). The cells are grown in RPMI 1640 (GIBCO®) supplemented with 10% heat inactivated FBS and 0.1 mg/ml penicillin/streptomycin. H358 cells are cultured in the growth phase and five thousand cells per well are plated in a black well clear round bottom 96-well ultra-low attachment surface plate (Corning® Cat 4520) with 80 µl/well of culture media. Cells are incubated overnight at 37° C. in a humidity chamber. 20 µl/well of serially diluted test compound is added to the plate which is then incubated for 96 hr. Plates are brought to RT and an equal volume of RT CellTiterGlo® 3D reagent is added. Plates are shaken at 750 RPM for 10 min at RT After a 1 hr incubation at RT to stabilize the signal, the luminescent signal is measured on the EnVision™ plate reader. The signal is converted to percent inhibition using the following equation: % Inhibition=100−[(Test Compound Signal−Median Minimum Signal)/(Median Maximum Signal−Median Minimum Signal)×100]. The Max Signal is a control well without inhibitor. The Minimum Signal is a control well containing a reference inhibitor sufficient to fully inhibit cell proliferation. The IC$_{50}$ is determined by fitting the percent inhibition at each inhibitor concentration to the four parameter nonlinear logistic equation using Genedata Screener®: y=(A+((B−A)/(1+((C/x)^D)))) where, y=% inhibition, A=minimum asymptote, B=maximum asymptote, C=relative IC$_{50}$ or the inhibitor concentration producing 50% inhibition within the fitted range of both asymptotes, and D=Hill Slope.

Compounds within the scope of this invention are evaluated in this assay substantially as described above. The compound of Example 1 exhibited a relative IC$_{50}$ in this assay less than 0.0116 µM. This data show that the compound of Example 1 inhibits the proliferation of H358 human lung cancer cells.

CellTiterGlo Cell Proliferation Assay

A panel of tumor cell lines harboring KRas G12C or other KRas mutations are collected (Table 6). All cell lines are from ATCC or other sources indicated.

Typically cells are cultured in RPMI1640 or Dulbecco's modified Eagle's medium (DMEM, GIBCO) supplemented with 10% FBS (GIBCO, Invitrogen). For 2D culture cells (4×10$^3$/well) maintained in growth medium described above, are plated onto 96 well tissue culture plates Corning® Cat. 3603) a day before the treatment. For 3D culture 8000 cells/well are seeded onto 96 well ultra-low attachment tissue culture plates (Corning, #3474). The cells are treated compound for 96 hr, and then are analyzed for viability using the CellTiterGlo® Luminescent Cell Viability Assay® (Promega #G7572 for 2D and Promega #G9683 for 3D cultures) according to manufacturer's instructions and an EnVision™ plate reader. Nonlinear regression and sigmoidal dose-response curves are used to calculate the half maximal inhibitory concentration (IC$_{50}$) with GraphPad Prism 4® software.

TABLE 6

In vitro anti-proliferation activities of Example 1 in a panel of KRas G12C mutation tumor cell lines

| Cell lines | KRas mutation | Cancer Type | IC50 (µM) in 2 D cell proliferation | IC50 (µM) in 3 D spheroid cell proliferation |
|---|---|---|---|---|
| EL3187 | G12C | Lung | 0.003 | 0.013 |
| Calu-1 | G12C | Lung | 0.024 (n = 3) | 0.001 |
| H358 | G12C | Lung | 0.041 (n = 5) | 0.026 (n = 2) |
| H23 | G12C | Lung | 0.080 | 0.031 |
| H2122 | G12C | Lung | 0.187 (n = 3) | 0.017 (n = 2) |
| H1373 | G12C | Lung | 0.209 | 0.020 |
| HCC-44 | G12C | Lung | 0.221 | nd |
| LXFA-983L | G12C | Lung | 1.339 (n = 4) | 0.050 |
| LU-99 | G12C | Lung | 1.568 | 0.659 |
| H1792 | G12C | Lung | 3.933 (n = 4) | 3.836 |
| H2030 | G12C | Lung | 6.881 (n = 3) | 0.003 |
| SW1573 | G12C | Lung | 16.723 | nd |
| D122-96 | G12C | Lung (mouse) | 0.126 (n = 3) | 0.069 (n = 3) |
| SW1463 | G12C | colon | 0.013 | nd |
| SW837 | G12C | Rectum | 0.169 (n = 4) | 0.126 |
| Miapaca-2 | G12C | Pancreas | 0.014 (n = 4) | 0.086 |
| UM-UC-3 | G12C | Bladder | 0.124 | 0.075 |
| SW756 | G12C | Cervix | 1.153 (n = 4) | 7.827 |
| Kyse-410 | G12C | Esophagus | 2.942 (n = 4) | 0.471 |
| A427 | G12D | lung | 10.130 | 18.58 (n = 2) |
| H460 | Q61H | lung | 11.557 | 6.073 |
| Calu-6 | Q61K | lung | 12.050 | 19.54 (n = 2) |
| H441 | G12V | lung | 16.484 | 7.888 |
| A549 | G12S | lung | 17.697 | 5.944 |
| H1975 | wild type | lung | 18.690 | 6.196 |
| HCC827 | wild type | lung | 18.926 | 4.629 | note: nd: not done; n: number of assays

The data indicate that the compound of Example 1 inhibits the growth of the KRas G12C mutant tumor cell lines listed in Table 6.

As summarized in Table 6, the compound of Example 1 exhibited anti-proliferation activities in most of the tumor cells with KRas G12C mutation in 2D and 3D culture conditions. In A549 cells with KRas G12S mutation, the compound of Example 1 exhibited little activity in either 2D or 3D assay, suggesting that Example 1 selectively inhibits tumor cells with KRas G12C mutation.

Inhibition of KRas G12C Pharmacodynamic (PD) Marker and Tumor Growth with H358 and H2122 Xenograph Models To evaluate in vivo target inhibition and anti-tumor efficacy of a compound, Human lung cancer cells, H358 or H2122 are implanted into nude mice xenograft tumor models. Either H358 or H2122 cells (10×10$^6$ in a 1:1 Matrigel® mix, 0.2 mL total volume) are implanted by subcutaneous injection in hind leg of nude female mice (Harlan Laboratories). A total of 5 mice each group are used for efficacy study, and a total of 3-4 mice each group are used for target engagement and PD study. Treatment is initiated with oral administration (gavage) of a test compound or vehicle (20% Captisol®, 25 mM phosphate, pH 2.0 in 0.2 mL volume when the tumor size reaches approximately 300 mg. Tumor growth and body weight are monitored over time to evaluate efficacy and signs of toxicity. Bidimensional measurements of tumors are performed twice a week and tumor volumes are calculated based on mid-axis length and mid-axis width. Tumor volume data are transformed to a log scale to equalize variance across time and treatment groups. The log volume data are analyzed with a two-way repeated measures analysis of variance by time and treatment using the mixed procedures in SAS software (version 8.2). The correlation model for the repeated measures is spatial power. Treated groups are compared to the control group at each time point. The mixed procedure is also used separately for each treatment group to calculate adjusted means and standard errors at each time point. Both analyses account for the autocorrelation within each animal. The adjusted means and standard errors are plotted for each treatment group versus time.

For in vivo target inhibition and PD analysis, tumors are ground by mortar and pestle on dry ice and tumor fragments are added to 800 μL of lysis buffer containing 1% Triton X100, 25 mM Tris pH 7.5, 150 mM NaCl, 1 mM EDTA, and 1 mM EGTA with Halt protease and phosphatase inhibitor cocktail (Thermo Scientific, cat. no. 1861281) in lysing matrix D tubes (MP Biomedical®, cat. no. 6913-500) with one additional large bead (MP Biomedical® ¼" ceramic sphere bead cat. no. 6540-412) per tube. Tumor fragments are homogenized in a Thermo Bio101® fast prep (FP120) at setting 4 for 15 min while cold for a total of 2 times. Lysates are spun at 14,000 rpm for 10 min at 4° C. to clarify. Protein estimation is done on the lysate supernatant using a BioRad Dc® protein assay and lysates are diluted in complete lysis/binding buffer from the Ras GTPase Chemi ELISA Kit® (Active Motif, cat. no. 52097). The active KRas ELISA was performed as follows: Glutathione-coated ELISA wells were incubated with diluted RAF1-GST in complete lysis/binding buffer for 1 hr at 4° C. with gentle agitation. Wells are washed 3 times with wash buffer and 100 μg of lysates are added to each well and incubated at RT for 1 hr with mild agitation. The wells are washed an additional 3 times, then primary antibody, diluted in antibody binding buffer, is added to each well. The plates are incubated for 1 hr. The wells are washed 3 more times before adding HRP-conjugated secondary antibody, diluted in antibody binding buffer, to each well. The plates are incubated at RT for 1 hr. ELISA wells are washed 4 times, chemiluminescent reagents is added and then luminescence is read. For pERK Meso Scale Discovery ELISA, 25 μg of protein containing 0.1% SDS is used; for pMEK Meso Scale Discovery ELISA, 50 μg of protein without SDS is used. Meso Scale Discovery Whole Cell Lysate Kits for pERK and pMEK are provided by Meso Scale Discovery.

Dose And Concentration Dependent In Vivo Target Inhibition And Pharmacodynamic Effects In Lung Cancer H388 Xenograft Model The compound of Example 1 is dosed in lung cancer H358 mouse xenograft model at a dose range from 1 to 100 mg/kg. The tumor samples are collected 4 hr post a single dose. The tumor lysates are prepared and the inhibition of pERK, pMEK, and active KRas is measured as described above. The results are provided in Table 7; the compound of Example 1 exhibited a dose dependent inhibiton of pERK, pMEK, and active KRas after a single dose treatment from 1 to 100 mg/kg at 4 hr. Based on this dose-dependent target inhibition, the doses to achieve 50% target inhibition ($TED_{50}$) is 11.2, 9.78 and 11.19 mg/kg for active KRas, pERK and pMEK, respectively. Additionally, the plasma exposures of the compound of Example 1 at different doses were measured using mass spectrum. The plasma concentrations to achieve 50% target inhibition ($TEC_{50}$) were 574.4, 474.4 and 515.3 nM for active KRas, pERK and pMEK, respectively.

TABLE 7

Dose Dependent Inhibition of pERK, pMEK And Active Kras in H358 Xenograft Mice Model

| Dose (mg/kg) | % Inhibition pERK | % Inhibition pMEK | % Inhibition Active KRas |
|---|---|---|---|
| Vehicle | 0 | 0 | 0 |
| 100 | 83.5 | 85.8 | 87.4 |
| 30 | 84.2 | 82.1 | 83.2 |
| 10 | 47.8 | 43.1 | 40.9 |
| 3 | 16.4 | 11.1 | −2.9 |
| 1 | 5.5 | −6.2 | −1.9 |

Time Dependent In Vivo Target Inhibition And Pharmacodynamic Effects In Lung Cancer H388 Xenograft Mouse Model The compound of Example 1 is also dosed at 10 and 30 mg/kg. After a single dose, the tumor samples are harvested at 2, 4, 8, 12 and 24 hr post doing. The tumor lysates are prepared and the inhibition of pERK, pMEK, and active KRas is measured as described above. The results are provided in Table 8. The compound of Example 1 exhibited a time dependent inhibiton of pERK, pMEK, and active KRas after a single dose treatment of 10 or 30 mg/kg. At 10 mg/kg, 61-83% pERK inhibition was observed from 2-12 hr, and the pERK inhibition decrease to 45% at 24 hr. For pMEK inhibition, 49-78% inhibition was observed from 2-12 hr, which decreased to 30% at 24 hr. For active Kras, 21-61% inhibition was achieved from 2-24 hr. At 30 mg/kg, 63-87% pERK inhibition, 35-89% pMEK inhibition, and 29-70% active KRas inhibition were achieved from 2-24 hr after a single dose.

TABLE 8

Time Dependent Inhibition of pERK, pMEK And Active KRas

| | Hour | % Inhibition pERK | % Inhibition pMEK | % Inhibition Active KRas |
|---|---|---|---|---|
| vehicle | 4 | 0 | 0 | 0 |
| 10 mg/kg | 2 | 61.7 | 49.2 | 26.1 |
| | 4 | 73.5 | 59.5 | 32.9 |
| | 8 | 69.2 | 62.4 | 30 |
| | 12 | 83 | 77.9 | 61.1 |
| | 24 | 45 | 30.4 | 21.5 |
| 30 mg/kg | 2 | 83.1 | 81.4 | 70.4 |
| | 4 | 87.3 | 89.3 | 65 |
| | 8 | 86.5 | 81.8 | 66.5 |
| | 12 | 77.4 | 65.8 | 28.7 |
| | 24 | 63.4 | 35 | 37.7 |

Dose And Time Dependent In Vivo Target Inhibition And Pharmacodynamic Effects In Lung Cancer H2122 Xenograft Mouse Model The compound of Example 1 is dosed at 10, 30, and 100 mg/kg. After a single dose, the tumor samples are harvested at different time points. The tumor lysates are prepared as described above. The inhibition of pERK, pMEK, and active KRas is measured as described above. As demonstrated in Table 9, the compound of Example 1 exhibited dose dependent inhibition of pERK, pMEK, and active KRas after a single dose treatment of 10, 30 or 100 mg/kg at 4 h. The inhibition of these PD markers increased by increasing dose from 10-100 mg/kg. Additionally, the compound of Example 1 exhibited a time-dependent target inhibition and PD effects in this model. At 10 mg/kg, 7-47% pERK inhibition, 0-60% pMEK inhibition, and 26-37% active KRas inhibition were observed from 2-12 hr. Inhibition of this PD marker decreased at 24 hr. At 30 mg/kg, 49-76% pERK inhibition, 45-78% pMEK inhibition, and 26-79% active KRas inhibition were achieved from 2-124 hr after a single dose. The inhibition of these PD markers were decreased at 24 h (Table 6).

TABLE 9

Dose and Time Dependent Inhibition of pERK, pMEK and Active KRas by compound Example 1 in Lung Cancer H2122 Xenograft Model

|  | Hour | % Inhibition pERK | % Inhibition pMEK | % Inhibition Active KRas |
|---|---|---|---|---|
| vehicle | 4 | 0 | 0 | 0 |
| 10 mg/kg | 2 | 46.8 | 45.9 | 25.8 |
|  | 4 | 47 | 60.4 | 32.3 |
|  | 8 | 34.5 | 25.7 | 34.7 |
|  | 12 | 7.2 | −0.4 | 37.1 |
|  | 24 | −2.8 | −8.4 | 16.7 |
| 30 mg/kg | 2 | 75.6 | 62.4 | 57.5 |
|  | 4 | 75.3 | 77.5 | 78.8 |
|  | 8 | 67.4 | 72.2 | 67 |
|  | 12 | 48.8 | 44.7 | 46.5 |
|  | 24 | 20.4 | −15.5 | 26.1 |
| 100 mg/kg | 4 | 79.1 | 79.7 | 90.6 |

Anti-Tumor Growth Activity in Lung Cancer H358 Xenograft Mouse Model

The anti-tumor activity of the compound of Example 1 is determined in a lung cancer H358 mouse xenograft model. H358 lung tumor cells ($10 \times 10^6$) are implanted by subcutaneous injection in hind leg of nude female mice (Taconic Biosciences). A total of 5 mice each group are used for efficacy study. Treatment is initiated with oral administration (gavage) of the test compound or vehicle (20% Captisol®, 25 mM phosphate, pH 2.0 in 0.2 mL volume once or twice daily for 28 days when the tumor size reaches approximately 300 mg. Tumor growth and body weight are monitored over time to evaluate efficacy and signs of toxicity as described above in the description on the Inhibition of KRas G12C Pharmacodynamic (PD) Marker and Tumor Growth with H358 and H2122 Xenograph Models. At 10 mg/kg once daily dosing schedule, 42.7% tumor growth inhibition was observed. At 10 mg/kg twice daily dosing schedule, −1.98% tumor regression was observed. At 30 mg/kg once daily or twice daily dosing schedules, −33.98% and −74.35% tumor progression was achieved, respectively. No significant animal body weight loss was observed through the whole study.

Anti-Tumor Growth Activity in Lung Cancer H2122 Xenograft Mouse Model

The anti-tumor activity of the compound of Example 1 is also determined in lung cancer H2122 xenograft model. H2122 lung tumor cells ($10 \times 10^6$) are implanted by subcutaneous injection in hind leg of nude female mice (Taconic Biosciences). A total of 5 mice each group are used for efficacy study. Treatment is initiated with oral administration (gavage) of the test compound or vehicle (20% Captisol®, 25 mM phosphate, pH 2.0 in 0.2 mL volume once or twice daily for 28 days when the tumor size reaches approximately 300 mg. Tumor growth and body weight are monitored over time to evaluate efficacy and signs of toxicity as described above in the description on the Inhibition of KRas G12C Pharmacodynamic (PD) Marker and Tumor Growth with H358 and H2122 Xenograph Models. When the compound of Example 1 was dosed at 30 mg/kg once daily or twice daily, 77.17% and 72.97% tumor growth inhibition was observed, respectively. At 100 mg/kg once daily dose schedule, 91.06% tumor inhibition was observed. No significant animal body weight loss was observed through the whole study.

Anti-Tumor Growth Activities in Other Lung Cancer Models and Xenograft Models of Colorectal, Pancreatic and Esophageal Cancers In addition to H358 and H2122 xenograft models, compound Example 1 is tested in many other xenograft or patient-derived xenograft (PDX) models of lung, colorectal, pancreatic, and esophageal cancer at different doses. The anti-tumor growth or regression activities of monotherapy were summarized in Table 10. As illustrated in Table 10, compound Example 1 demonstrated anti-tumor activities in all these models from 5 to 100 mg/kg, suggesting that Example 1 is active against cancers with KRas G12C mutation including lung, colorectal, pancreatic, and esophageal cancer.

TABLE 10

Anti-Tumor Growth Activity by Compound Example 1 in 28 Day Lung, Colorectal, Pancreatic and Esophageal Cancer Xenograft or PDX Models.

| Xenograft/PDX models | Tissue | Tumor Growth Inhibition (%) or Regression (−%) | | | | | | | | | | |
|---|---|---|---|---|---|---|---|---|---|---|---|---|
|  |  | 5 mg/kg | | 10 mg/kg | | 15 mg/kg | | 20 mg/kg | 30 mg/kg | | 50 mg/kg | 100 mg/kg | |
|  |  | QD | BID | QD | BID | QD | BID | QD | QD | BID | QD | QD | BID |
| H358 | Lung | nd | nd | 42.7 | −1.98 | nd | nd | nd | −33.98 | −74.35 | nd | nd | nd |
| H2122 | Lung | nd | nd | nd | nd | nd | nd | nd | 77.2 | 72.97 | nd | 91.1 | nd |
| H1373 | Lung | nd | nd | nd | nd | nd | −60 | nd | −52.4 | −71.6 | nd | nd | nd |
| H2030 | Lung | nd | nd | nd | nd | nd | 82 | nd | 75.1 | 91.9 | nd | nd | nd |
| HCC44 | Lung | nd | nd | nd | nd | nd | 93.4 | nd | 85.4 | −16.5 | nd | nd | nd |
| EL3187 (PDX) | Lung | nd | nd | nd | nd | nd | nd | nd | −100 | −100 | nd | −100 | −100 |
| EL3187 (PDX) | Lung | 94 | −65 | nd | nd | −75 | −80 | nd | −85.4 | −92.5 | nd | nd | nd |

TABLE 10-continued

Anti-Tumor Growth Activity by Compound Example 1 in 28 Day Lung,
Colorectal, Pancreatic and Esophageal Cancer Xenograft or PDX Models.

| Xenograft/ PDX models | Tissue | 5 mg/kg QD | 5 mg/kg BID | 10 mg/kg QD | 10 mg/kg BID | 15 mg/kg QD | 15 mg/kg BID | 20 mg/kg QD | 30 mg/kg QD | 30 mg/kg BID | 50 mg/kg QD | 100 mg/kg QD | 100 mg/kg BID |
|---|---|---|---|---|---|---|---|---|---|---|---|---|---|
| EL2661 (PDX) | Lung | nd | nd | 46.5 | nd | nd | nd | 58.6 | 97.6 | | −8.6 | nd | nd |
| SW837 | Colorectal | nd | nd | nd | nd | nd | −17 | nd | −10.8 | −46.1 | nd | nd | nd |
| SW1463 | Colorectal | nd | nd | nd | nd | nd | −27 | nd | −13.9 | −47.9 | nd | nd | nd |
| MiaPaca-2 | Pancreatic | nd | nd | 44.4 | 75.48 | nd | nd | nd | 95.6 | −49.6 | nd | nd | nd |
| KYSE-410 | Esophageal | nd | nd | nd | nd | nd | 21.2 | nd | 74.5 | −9 | nd | nd | nd | note:
nd: not done
Positive numbers indicate percentage tumor growth inhibition, and negative numbers indicate percentage tumor regression.

Combination Efficacy with CDK4 and CDK6 Inhibitor Abemaciclib, EGFR Small Molecule Inhibitors or EGFR Monoclonal Antibody Cetuximab In addition to monotherapy, compound Example 1 is accessed for its combination efficacy with other targeted therapies, such as CDK4 and CDK6 inhibitor abemaciclib, EGFR small molecule inhibitor erlotinib and EGFR monoclonal antibody cetuximab. Cell lines for this study are obtained from ATCC and grown under ATCC recommended conditions, except for LXFA-983L, which is obtained from Oncotest/Charles Rivers Laboratories, Wilmington, Mass. and D122-96, which is obtained from L. Eisenbach (Weizman Institute of Science, Rehovot, Israel)—both grown under recommended conditions. All cell lines have a KRAS G12C mutation. The proliferation assay is performed as a 4 day growth assay using Cell TiterGlo® as the readout. Briefly, cells are plated in 96-well cell culture plates and allowed to adhere overnight at 37° C. The following day, cells are treated with compounds, either single treatments or combination treatments. First, the testing compounds are serially diluted in DMSO, followed by dilution into media as a 5× concentration with 1% DMSO, and finally added to cells in media to dilute to 1×. The cells are incubated at 37° C. for 4 more days. At the end of the incubation period, Cell TiterGlo® reagent is mixed and added to the wells. After 10 minutes, the luminescence is read by a Perkin Elmer Envision instrument. Absolute IC$_{50}$ values generated by a 4-parameter logistics model for the single and combination treatments are generated, followed by combination indexes for each combination treatment and cell line. The combination IC$_{50}$ values are adjusted based on the total concentration of each compound when added together. (Example: for a 1:1 concentration ratio of compound 1 and compound 2, the combination IC$_{50}$ is increased by a factor of 2). The combination index (CI) measures the degree to which the potency of a combination therapy differs from the expected-if-additive potency and is based on the Loewe definition of additivity.

$$CI = \frac{C_{A,y}}{IC_{A,y}} + \frac{C_{B,y}}{IC_{B,y}}$$

Where
$C_{Ay}$ and $C_{By}$ are the concentrations of therapies A and B that produce an effect, y, when given in combination $IC_{Ay}$ and $IC_{By}$ are the concentrations of A and B that produce an effect, y, when given individually The biological interpretation of the combination index is as follows: synergistic if the combination index <0.5, additive if the combination index is between 0.5 and 2, and antagonistic if the combination index is >2.

As shown in Table 11, combination of Example 1 and abemaciclib has additive or synergistic efficacy in inhibiting tumor cells with KRas G12C mutation. Among 16 cell lines tested, 11 cell lines have additive effects, and 5 cell lines have synergistic effects based on combination index, suggesting that combination of Example 1 and abemaciclib may provide benefit to cancer patients with KRas G12C mutation.

TABLE 11

In vitro anti-proliferation activities of Example 1 in Combination with CDK4 and CDK6 Inhibitor abemaciclib in a panel of KRas G12C mutation tumor cell lines

| Cell Line | Example 1 Absolute IC$_{50}$ (μM) | Abemaciclib Absolute IC$_{50}$ (μM) | Example 1 + Abemaciclib Absolute IC$_{50}$ (μM) | Example 1 + Abemaciclib Combination index (mean) |
|---|---|---|---|---|
| SW1463 | 0.0141 | 0.3277 | 0.01973 | 0.72696 |
| Calu-1 | 0.0145 | >10 | <0.006 | 0.5774 |
| MIA Paca-2 | 0.022 | 0.7548 | 0.02555 | 0.58442 |
| H358 | 0.0419 | 1.2282 | 0.05823 | 0.71787 |
| SW837 | 0.1012 | 3.5944 | 0.11775 | 0.59297 |
| D122-96 | 0.1245 | 5.0483 | 0.13213 | 0.54265 |
| H1373 | 0.1326 | >10 | 0.51073 | 1.934 |
| H23 | 0.2353 | 4.9715 | 0.22485 | 0.50279 |
| H1792 | 0.3372 | 1.0984 | 0.21347 | 0.4134 |
| KYSE-410 | 0.7622 | 3.0066 | 0.54635 | 0.43791 |
| SW756 | 0.8646 | 4.9808 | 0.81149 | 0.57949 |
| H2030 | 1.6866 | 9.034 | 4.43716 | 1.56279 |
| UM-UC-3 | 1.8347 | 1.7175 | 0.52266 | 0.30115 |
| LXFA-983L | 2.5915 | >10 | 2.14941 | 0.4404 |
| H2122 | 2.8704 | 0.5475 | 0.66374 | 0.71868 |
| SW1573 | >10 | 0.996 | 0.44059 | 0.22119 |

As shown in Table 12, combination of Example 1 and EGFR small molecule inhibitor erlotinib has additive or synergistic efficacy in inhibiting tumor cells with KRas G12C mutation. Among 16 cell lines tested, 11 cell lines have additive effects, 5 cell lines have synergistic effects, and 1 cell line has no effect based on combination index, suggesting that combination of Example 1 and erlotinib may provide benefit to cancer patients with KRas G12C mutation.

TABLE 12

In vitro anti-proliferation activities of Example 1 in Combination with EGFR Small Molecule Inhibitor Erlotinib in a panel of KRas G12C mutation tumor cell lines

| Cell Line | Example 1 Absolute $IC_{50}$ (µM) | Erlotinib Absolute $IC_{50}$ (µM) | Example 1 + Erlotinib Absolute $IC_{50}$ (µM) | Example 1 + Erlotinib Combination index (mean) |
|---|---|---|---|---|
| SW1463 | 0.014 | 0.446 | 0.022 | 0.821 |
| Calu-1 | 0.021 | >10 | 0.036 | 0.814 |
| MIA Paca-2 | 0.019 | >10 | <0.006 | 0.999 |
| H358 | 0.051 | 0.247 | 0.086 | 1.009 |
| SW837 | 0.164 | >10 | 0.17 | 0.519 |
| D122-96 | 0.111 | >10 | 0.195 | 0.873 |
| H1373 | 1.862 | >10 | 2.258 | 0.323 |
| H23 | 0.295 | >10 | 0.155 | 0.888 |
| H1792 | 3.007 | >10 | 3.588 | 0.745 |
| KYSE-410 | 1.586 | 0.469 | 0.91 | 1.227 |
| SW756 | 0.264 | >10 | 0.139 | 0.262 |
| H2030 | >10 | 1.477 | 3.280 | 1.141 |
| UM-UC-3 | 3.645 | >10 | 3.244 | 0.453 |
| LXFA-983L | 4.715 | 2.820 | 0.665 | 0.189 |
| H2122 | 2.391 | 0.352 | 0.492 | 0.794 |
| SW1573 | >10 | >10 | NA | NA |

As shown in Table 13, combination of Example 1 and EGFR monoclonal antibody cetuximab generally has additive or synergistic efficacy in inhibiting tumor cells with KRas G12C mutation. Among 16 cell lines tested, 6 cell lines have additive effects, 7 cell lines have synergistic effects, 2 cell lines have antagonistic effects, and 1 cell line has no effect based on combination index, suggesting that combination of Example 1 and cetuximab may provide benefit to most of cancer patients with KRas G12C mutation.

TABLE 13

In vitro anti-proliferation activities of Example 1 in Combination with EGFR Monoclonal Antibody Cetuximab in a panel of KRas G12C mutation tumor cell lines

| Cell Line | Example 1 Absolute $IC_{50}$ (µM) | Cetuximab Absolute $IC_{50}$ (µg/mL)) | Example 1 + Cetuximab Absolute $IC_{50}$ (µM) | Example 1 + Cetuximab Potentiation index (mean) |
|---|---|---|---|---|
| SW1463 | 0.0141 | >20 | 0.00553 | 0.07649 |
| Calu-1 | 0.0145 | >20 | <0.003 | 0.4006 |
| MIA Paca-2 | 0.022 | >20 | 0.01931 | 0.84494 |
| H358 | 0.0419 | >20 | 0.00578 | 0.12504 |
| SW837 | 0.1012 | >20 | 0.01254 | 0.11803 |
| D122-96 | 0.1245 | >20 | 0.09372 | 0.75219 |
| H1373 | 0.1326 | >20 | 0.97025 | 6.7919 |
| H23 | 0.2353 | >20 | 0.19644 | 0.84001 |
| H1792 | 0.3372 | >20 | 0.65556 | 1.77915 |
| KYSE-410 | 0.7622 | >20 | 1.02012 | 1.10193 |
| SW756 | 0.8646 | >20 | 0.12534 | 0.13355 |
| H2030 | 1.6866 | >20 | 7.73078 | 6.3229 |
| UM-UC-3 | 1.8347 | >20 | 1.44949 | 0.6735 |
| LXFA-983L | 2.5915 | >20 | 0.02627 | 0.011 |
| H2122 | 2.8704 | >20 | 0.22727 | 0.07545 |
| SW1573 | >10 | >20 | >10 | NA |

To further confirm the additive or synergistic effects of Example 1 in combination with abemaciclib, EGFR small molecule inhibitor, or EGFR monoclonal antibody cetuximab, in vivo combination studies are conducted in 6 xenograft or PDX models (3 lung, 2 colorectal and 1 pancreatic). As shown in Table 14, combination of Example 1 and abemaciclib has better anti-tumor activities than monotherapy in all 6 models tested. In many cases, significant tumor regression is achieved by this combination, suggesting that combination of Example 1 and abemaciclib has potential benefit for cancer patients with KRas G12C mutation.

Additionally, combination of Example 1 and EGFR monoclonal antibody cetuximab was also evaluated in 4 xenograft or PDX models. As summarized in Table 14, combination of Example 1 with cetuximab demonstrated better tumor growth regression than monotherapy in two colorectal xenograft models (SW837, SW1463), suggesting that combination of Example 1 with EGFR monoclonal antibody cetuximab may have benefit for colorectal cancer patients with KRas G12C mutation.

TABLE 14

In Vivo Anti-Tumor Activities of Example 1 in Combination with Abemaciclib or Cetuximab in Tumor Xenograft or PDX Models

| Xenograft/ PDX | Tumor Type | Example 1 (mg/kg) 30 QDx28 | Example 1 (mg/kg) 100 QDx28 | Abemaciclib 50 mg/kg QDx28 | Example 1 + Abemaciclib 30 + 50 mg/kg QDx28 | Cetuximab 20 mg/kg BIWx4 | Example 1 + Cetuximab 30 + 20 mg/kg QDx28/ BIWx4 |
|---|---|---|---|---|---|---|---|
| H2122 | Lung | 77.2 | | 79.3 | −7.5 | | |
| H2122 | Lung | | −1.4 | 79.1 | −23.4 | | |
| H358 | Lung | −33.4 | | | −73.5 | | |
| SW837 | Colorectal | −51.8 | | −2.13 | −59.88 | 58.49 | −68.51 |
| SW1463 | Colorectal | −21.4 | | 55.1 | −32.6 | 81.1 | −45.8 |
| MiaPaca-2 | Pancreatic | 91.22 | | 46.88 | −40.27 | −20.8 | 93.09 |

Combination of Example 1 and EGFR small molecule inhibitor, erlotinib or afatinib, was also evaluated in EL3187 lung cancer PDX model. As summarized in Table 15, combination of Example 1 with erlotinib or afatinib demonstrated significant tumor growth regression and much better anti-tumor activity than monotherapy, suggesting that combination of Example 1 with EGFR small molecule inhibitor may have significant benefit for lung cancer patients with KRas G12C mutation.

TABLE 15

In Vivo Anti-Tumor Activities of Example 1 in Combination EGFR Small Molecule Inhibitor in PDX Model

| Xenograft/ PDX | Tumor Type | Example 1 (mg/kg) 5 QDx28 | Erlotinib 25 mg/kg QDx28 | Example 1 + Erlotinib 5 + 25 mg/kg QDx28 | Afatinib 25 mg/kg QDx28 | Example 1 + Afatinib 5 + 25 mg/kg QDx28 |
|---|---|---|---|---|---|---|
| EL3187 (PBX) | Lung | 94.8 | 7.8 | −98.8 | 17.1 | −69.6 |

Combination Efficacy with Immuno-Therapies, Anti-PD-1 or Anti-PD-L1 Antibody

A mouse syngeneic model is used to evaluate the effects of KRas G12C inhibition and immuno-therapy combination. In this model, the KRas G12D mutation is converted to KRas G12C mutation by CRISPR knock-in in the CT-26 cell line, a mouse colorectal tumor cell line. The KRas G12C knock-in is confirmed by genetic and functional characterization. The engineered cell line is named CT-26-H4/KRas G12C. These cells are implanted to the Balb/c mice, and the compound treatment is started 6 days post tumor cell implantation. In this study, Example 1 is combined with either anti-PD-L1 or anti-PD-1 antibody with the dose schedule listed in Table 18. PD-1 and PD-L1 inhibitors are known in the art and include durvalumab, pembrolizumab, and nivolumab. As shown in Table 16, Example 1 demonstrates significant single agent activity with an average of 96% tumor growth inhibition and 10% (1 out of 10 animals) complete response (CR) at the end of 3 week dose. Anti-PD-L1 antibody shows 38% tumor growth inhibition with no complete response, and anti-PD-1 antibody shows 82% tumor growth inhibition and 10% complete response. However, combination of Example 1 with either anti-PD-L1 or anti-PD-1 antibody achieves significantly better anti-tumor activity. At the end of 3 week dose, the combination with PD-L1 or PD-1 shows −56% and −51% tumor regression, and 80% and 89% complete response, respectively. After 3 weeks, compound treatment is stopped and all tumors in monotherapy groups with the exception of 1 animal in the anti-PD-1 group started to regrow. However, the tumors in the two combination groups have no signs of regrowth. 40 days post last dose, the combination groups maintain 80 and 89% complete response, indicating that the tumors in the combination groups are eliminated. These results suggest that Example 1 combination with either anti-PD-L1 or anti-PD-1 antibody may have significant benefit for cancer patients with KRas G12C mutation.

TABLE 16

In Vivo Anti-Tumor Activities of Example 1 in Combination with Immuno-Therapy (Anti-PD-1 or Anti-PD-L1 antibody) in CT-26-H4/KRas G12C Syngeneic Model

| Treatment | Dose Schedule | End of treatment at day 28 % Tumor Growth Inhibition | End of treatment at day 28 % Regression | End of treatment at day 28 Complete Response (CR)/ group mice (% CR) | 40 days post treatment Complete Response (CR)/ group mice (% CR) |
|---|---|---|---|---|---|
| Vehicle | BID × 21 | 0 | | 0/10 (0%) | 0/10 (0%) |
| Example 1 | 30 mg/kg BID × 21, PO | 96 | | 1/10 (10%) | 0/10 (0%) |
| PD-L1 antibody (LSN3428712) | 500 ug/mouse, Q7D × 3, IP | 38 | | 0/10 (0%) | 0/10 (0%) |
| PD-1 antibody (RMP1-14) | 250 ug/mouse, BIW × 3, IP | 82 | | 1/10 (10%) | 1/10 (10%) |

TABLE 16-continued

In Vivo Anti-Tumor Activities of Example 1 in Combination with Immuno-
Therapy (Anti-PD-1 or Anti-PD-L1 antibody) in CT-26-H4/KRas G12C Syngeneic Model

| | | End of treatment at day 28 | | | 40 days post treatment |
|---|---|---|---|---|---|
| Treatment | Dose Schedule | % Tumor Growth Inhibition | % Regression | Complete Response (CR)/ group mice (% CR) | Complete Response (CR)/ group mice (% CR) |
| Example 1 + PD-L1 antibody | 30 mg/kg BID × 21, PO; 500 ug/mouse, Q7D × 3, IP | | −56 | 8/10 (80%) | 8/10 (80%) |
| Example 1 + PD-1 antibody | 30 mg/kg BID × 21, PO; 250 ug/mouse, BIW × 3, IP | | −51 | 8/9 (89%) | 8/9 (89%) |

What is claimed is:

1. A compound of the formula:

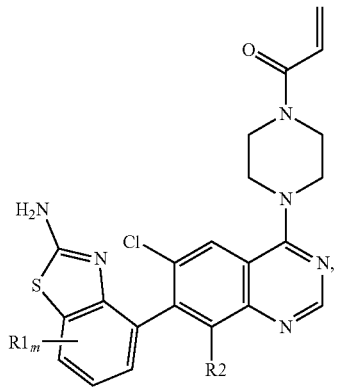

wherein m is 0-2;

each R1 is F; and

R2 is selected from: H, F, and Cl;

or a pharmaceutically acceptable salt thereof.

2. The compound according to claim 1 selected from:

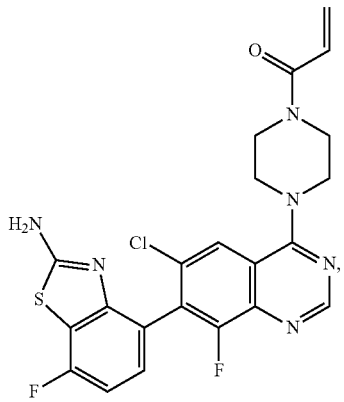 [SMILES: C=CC(=O)N1CCN(c2ncnc3c(F)c(-c4ccc(F)c5sc(N)nc45)c(Cl)cc23)CC1]

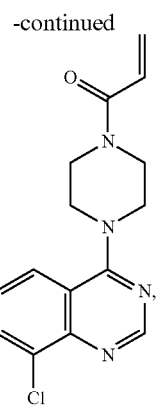

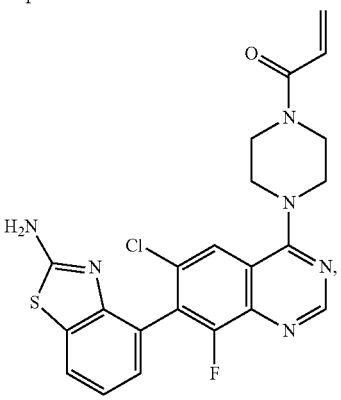

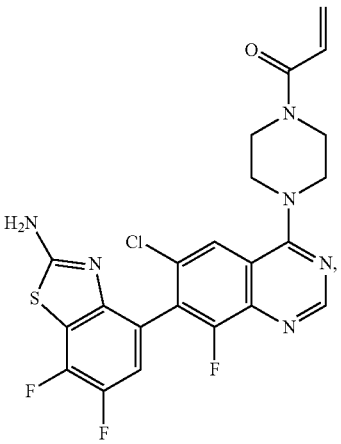

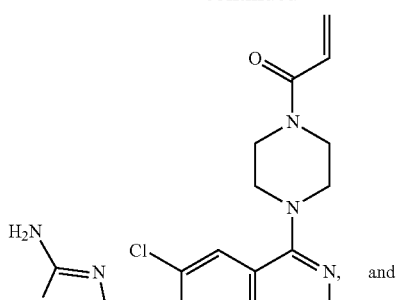

and

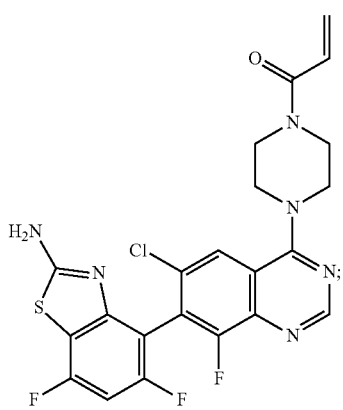

or a pharmaceutically acceptable salt thereof.

3. The compound according to claim 2 selected from:

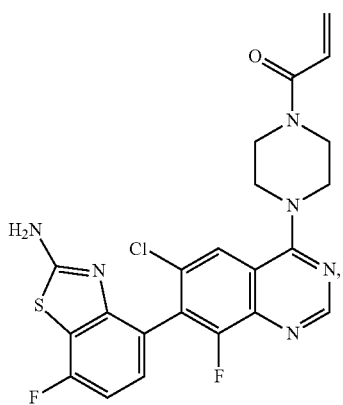 [SMILES: C=CC(=O)N1CCN(c2ncnc3c(F)c(-c4ccc(F)c5sc(N)nc45)c(Cl)cc23)CC1]

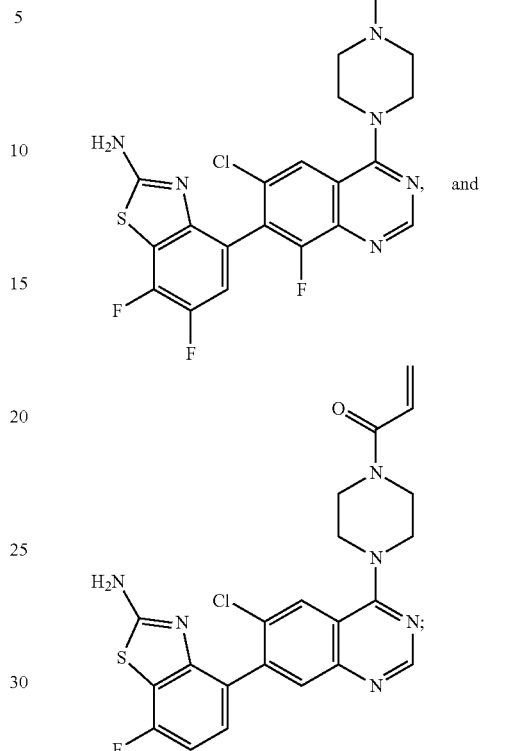

or a pharmaceutically acceptable salt thereof.

4. The compound which is:

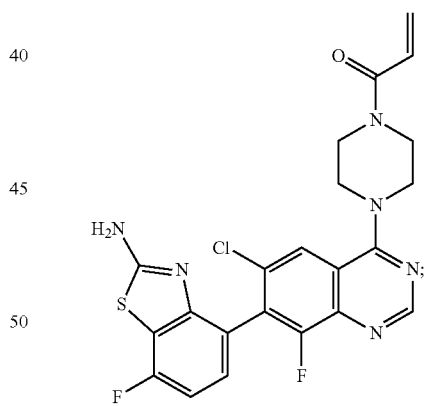

or a pharmaceutically acceptable salt thereof.

5. The compound according to claim 4 which is 1-{4-[7-(2-amino-7-fluoro-1,3-benzothiazol-4-yl)-6-chloro-8-fluoroquinazolin-4-yl]piperazin-1-yl}prop-2-en-1-one hemi-malonate.

6. The compound according to claim 4 which is 1-{4-[7-(2-amino-7-fluoro-1,3-benzothiazol-4-yl)-6-chloro-8-fluoroquinazolin-4-yl]piperazin-1-yl}prop-2-en-1-one mesylate.

7. The compound according to claim 5 which is crystalline 1-{4-[7-(2-amino-7-fluoro-1,3-benzothiazol-4-yl)-6-chloro-8-fluoroquinazolin-4-yl]piperazin-1-yl}prop-2-en-1-one hemi-malonate.

8. The compound according to claim 7 which is crystalline 1-{4-[7-(2-amino-7-fluoro-1,3-benzothiazol-4-yl)-6-chloro-8-fluoroquinazolin-4-yl]piperazin-1-yl}prop-2-en-1-one hemi-malonate characterized by an X-ray powder diffraction pattern having characteristic peaks using CuKα radiation, in 2θ±0.2°, occurring at 5.4° in combination with one or more of the peaks selected from the group consisting of 13.5°, 7.1°, and 23.0°.

9. The compound according to claim 6 which is crystalline 1-{4-[7-(2-amino-7-fluoro-1,3-benzothiazol-4-yl)-6-chloro-8-fluoroquinazolin-4-yl]piperazin-1-yl}prop-2-en-1-one mesylate.

10. The compound according to claim 9 which is crystalline 1-{4-[7-(2-amino-7-fluoro-1,3-benzothiazol-4-yl)-6-chloro-8-fluoroquinazolin-4-yl]piperazin-1-yl}prop-2-en-1-one mesylate characterized by a X-ray powder diffraction pattern having characteristic peaks using CuKα radiation, in 2θ±0.2°, occurring at 6.1° in combination with one or more of the peaks selected from the group consisting of 21.3°, 18.6°, and 19.8°.

11. A pharmaceutical composition comprising a compound of the formula:

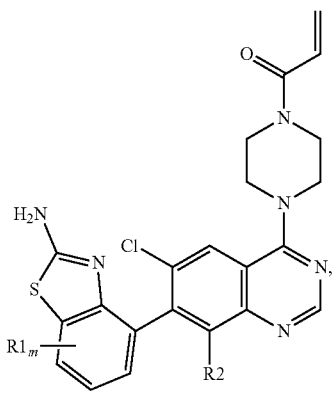

wherein m is 0-2;
each R1 is F; and
R2 is selected from: H, F, and Cl;
or a pharmaceutically acceptable salt thereof; and a pharmaceutically acceptable carrier, diluent or excipient.

12. The pharmaceutical composition according to claim 11 wherein the compound is:

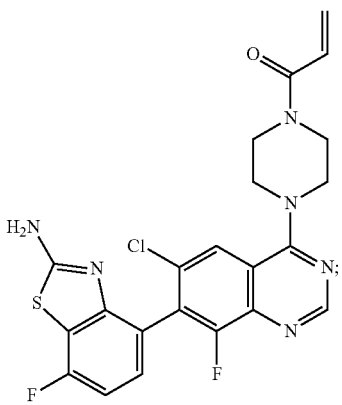 [SMILES: C=CC(=O)N1CCN(c2ncnc3c(F)c(-c4ccc(F)c5sc(N)nc45)c(Cl)cc23)CC1]

or a pharmaceutically acceptable salt thereof.

13. The pharmaceutical composition according to claim 12 wherein the pharmaceutically acceptable salt is a mesylate salt.

14. A method of treating a patient for cancer, comprising administering to a patient in need thereof, an effective amount of a compound of the formula:

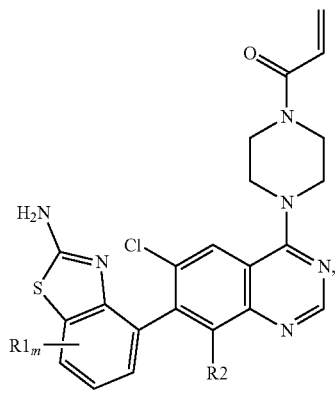

wherein m is 0-2;
each R1 is F; and
R2 is selected from: H, F, and Cl;
or a pharmaceutically acceptable salt thereof, wherein the cancer is lung cancer, colorectal cancer, pancreatic cancer, bladder cancer, cervical cancer, or esophageal cancer.

15. The method according to claim 14 wherein the compound is:

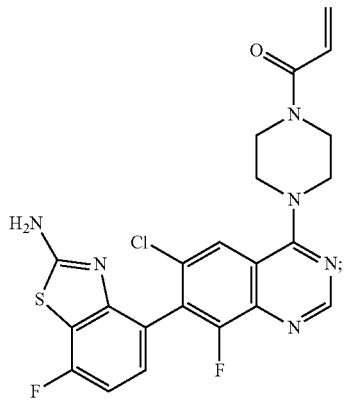

or a pharmaceutically acceptable salt thereof.

16. The method according to claim 15 wherein the pharmaceutically acceptable salt is a mesylate salt.

17. The method according to claim 15 wherein the cancer is non-small cell lung cancer, wherein one or more cells express KRas G12C mutant protein.

18. The method according to claim 15 wherein the cancer is colorectal cancer wherein one or more cells express KRas G12C mutant protein.

19. The method according to claim 15 wherein the cancer is pancreatic cancer, wherein one or more cells express KRas G12C mutant protein.

20. The method according to claim 15 wherein the patient has a cancer that was determined to have one or more cells expressing the KRas G12C mutant protein prior to administration of the compound or a pharmaceutically acceptable salt thereof.

21. The method according to claim 15 which further comprises simultaneous, separate, or sequential administration of an effective amount of abemaciclib or a pharmaceutically acceptable salt thereof.

22. The method according to claim 15 which further comprises simultaneous, separate, or sequential administration of an effective amount of an EGFR inhibitor or a pharmaceutically acceptable salt thereof.

23. The method according to claim 22 wherein the EGFR inhibitor is erlotinib or a pharmaceutically acceptable salt thereof.

24. The method according to claim 22 wherein the EGFR inhibitor is afatinib or a pharmaceutically acceptable salt thereof.

25. The method according to claim 22 wherein the EGFR inhibitor is cetuximab.

26. The method according to claim 15 which further comprises simultaneous, separate, or sequential administration of an effective amount of an anti-PD-1 antibody or an anti-PDL-1 antibody.

* * * * *